United States Patent

Mihayashi et al.

[11] Patent Number: 5,312,726
[45] Date of Patent: * May 17, 1994

[54] SILVER HALIDE COLOR PHOTOGRAPHIC MATERIAL

[75] Inventors: Keiji Mihayashi; Seiji Ichijima; Toshio Kawagishi; Naoki Saito; Masuji Motoki, all of Kanagawa, Japan

[73] Assignee: Fuji Photo Film Co., Ltd., Kanagawa, Japan

[ * ] Notice: The portion of the term of this patent subsequent to Nov. 19, 2008 has been disclaimed.

[21] Appl. No.: 666,995

[22] Filed: Mar. 11, 1991

[30] Foreign Application Priority Data

Mar. 12, 1990 [JP] Japan ................................. 2-60735
Jul. 17, 1990 [JP] Japan ................................. 2-188240

[51] Int. Cl.⁵ ................................................ G03L 7/36
[52] U.S. Cl. ...................................... 430/544; 430/557; 430/957
[58] Field of Search ............ 430/544, 557, 556, 558 R, 430/957

[56] References Cited

U.S. PATENT DOCUMENTS 2,359,274  9/1944  Wilson ................................. 430/556
2,435,173  1/1948  Bavley ................................. 430/556
5,066,576  11/1991 Ichijima et al. ..................... 430/557

FOREIGN PATENT DOCUMENTS 0336411  10/1989  European Pat. Off. .
0346899  12/1989  European Pat. Off. .
52-82423  7/1977   Japan .

Primary Examiner—Richard L. Schilling
Attorney, Agent, or Firm—Birch, Stewart, Kolasch & Birch

[57] ABSTRACT

A silver halide color light-sensitive material including a support having thereon at least one hydrophilic colloidal layer is disclosed, wherein the hydrophilic colloidal layer contains a DIR coupler represented by formula (I):

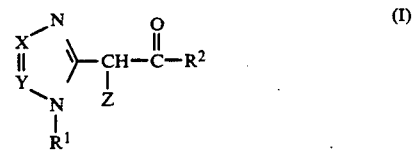

wherein $R^1$ represents a hydrogen atom, an aliphatic group, an aromatic group, or a heterocyclic group; $R^2$ represents an organic group; X and Y each represent —N= or

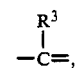

wherein $R^3$ represents a hydrogen atom, a halogen atom, a cyano group, a nitro group, an amino group, an acyl group, an acylamino group, a carbamoyl group, a carbamoylamino group, a sulfonyl group, a sulfonylamino group, a sulfamoyl group, a sulfamoylamino group, an alkoxy group, an aryloxy group, an alkoxycarbonyl group, an aryloxycarbonyl group, a hydroxyl group, a sulfenyl group, a sulfinyl group, an aliphatic group, an aromatic group, or a heterocyclic group; and Z represents a releasable group which is released on reacting with an oxidation product of an aromatic primary amine developing agent to become a development inhibitor or a precursor thereof and which diffuses into a color developing solution and then decomposes to a compound having no substantial influence on photographic properties.

14 Claims, No Drawings

SILVER HALIDE COLOR PHOTOGRAPHIC MATERIAL

FIELD OF THE INVENTION

This invention relates to a color photographic material having excellent sharpness and color reproducibility.

BACKGROUND OF THE INVENTION

In the field of color photography, extensive studies have been conducted in an attempt to improve sharpness and color reproducibility. Development inhibitor-releasing couplers (called DIR couplers) have been the subject of some of these studies. As a result, various DIR couplers have been discovered. For example, known DIR couplers include those described in U.S. Pat. Nos. 3,227,554, 3,701,783, 3,615,506, and 3,617,291, and JP-A-52-82423 (the term "JP-A" as used herein means an "unexamined published Japanese patent application"). With these DIR couplers, though, the development inhibitor which is released from the light-sensitive material on color development and diffused into a processing solution accumulates in the processing solution, and the processing solution comes to have an unfavorable development inhibitory effect as a result.

In order to overcome this problem, there has been a need to use a DIR coupler releasing a development inhibitor which, after diffusing into a color developing solution, is decomposed to a substance having no substantial adverse effect on photographic properties. Such DIR couplers have been described, for example, in U.S. Pat. No. 4,477,563. These couplers cause no contamination of the color developing solution, so they are suitable for use in continuous processing. In particular, malondianilide couplers disclosed in U.S. Pat. No. 4,477,563 have been used as DIR couplers because of their high coupling activity. However, the dye image produced from malondianilide couplers has poor resistance to humidity and heat. Some improvement has been made, as exemplified by the couplers disclosed in JP-A-2-28645, but the effects attained are insufficient and still require further improvement. In particular, when a DIR coupler is present in a photographic material in an increased amount, the dye image produced therefrom must have sufficient stability for maintaining its density.

SUMMARY OF THE INVENTION

An object of the present invention is to provide a highly sensitive color photographic material having excellent sharpness and color reproducibility and containing a DIR coupler which is capable of coupling with an oxidation product of a color developing agent to produce a dye having sufficient stability without causing contamination of the developing solution.

The above object of the present invention is accomplished by a silver halide color light-sensitive material comprising a support having thereon at least one hydrophilic colloidal layer which contains a DIR coupler represented by formula (I):

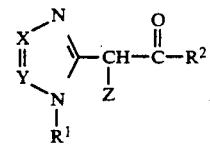

wherein $R^1$ represents a hydrogen atom, an aliphatic group, an aromatic group, or a heterocyclic group; $R^2$ represents an organic group; X and Y each represent —N= or

wherein $R^3$ represents a hydrogen atom, a halogen atom, a cyano group, a nitro group, an amino group, an acyl group, an acylamino group, a carbamoyl group, a carbamoylamino group, a sulfonyl group, a sulfonylamino group, a sulfamoyl group, a sulfamoylamino group, an alkoxy group, an aryloxy group, an alkoxycarbonyl group, an aryloxycarbonyl group, a hydroxyl group, a sulfenyl group, a sulfinyl group, an aliphatic group, an aromatic group, or a heterocyclic group; and Z represents a releasable group which is released on reacting with an oxidation product of an aromatic primary amine developing agent to become a development inhibitor or a precursor thereof and which diffuses into a color developing solution and then decomposes to a compound having no substantial influence on photographic properties.

DETAILED DESCRIPTION OF THE INVENTION

In formula (I), the aliphatic group as represented by $R^1$ or $R^3$ is a saturated or unsaturated, acyclic or cyclic, straight chain or branched, and substituted or unsubstituted aliphatic hydrocarbon group having from 1 to 40 carbon atoms, preferably from 1 to 22 carbon atoms. Typical examples of such an aliphatic group are methyl, ethyl, propyl, isopropyl, butyl, t-butyl, isobutyl, t-amyl, hexyl, cyclohexyl, 3-ethylhexyl, octyl, 1,1,3,3-tetramethylbutyl, decyl, dodecyl, hexadecyl, octadecyl, vinyl, allyl, benzyl, and phenethyl groups.

The aromatic group as represented by $R^1$ or $R^3$ is an aromatic group having from 6 to 20 carbon atoms, preferably a substituted or unsubstituted phenyl or a substituted or unsubstituted naphthyl group.

The heterocyclic group as represented by $R^1$ or $R^3$ is a substituted or unsubstituted and, preferably, 3- to 8-membered heterocyclic group containing from 1 to 20 carbon atoms, preferably from 1 to 7 carbon atoms, and having a hetero atom selected from a nitrogen atom, an oxygen atom, and a sulfur atom. Typical examples of such a heterocyclic group are 2-pyridyl, 4-pyridyl, 2-thienyl, 2-furyl, 2-imidazolyl, pyrazinyl, 2-pyrimidinyl, 1-imidazolyl, 1-indolyl, 1,3,4-thiadiazol-2-yl, benzoxazol-2-yl, 2-quinolyl, 2,4-dioxo-1,3-imidazolidin-3-yl, succinimido, phthalimido, 1,2,4-triazol-2-yl, and 1-pyrazolyl groups.

The halogen atom as represented by $R^3$ includes a fluorine atom, a chlorine atom, a bromine atom, and an iodine atom, with a chlorine atom being preferred.

The amino group as represented by $R^3$ includes methylamino, ethylamino, and anilino groups.

The acyl group as represented by $R^3$ includes acetyl, propanoyl, butanoyl, octanoyl, dodecanoyl, benzoyl, furoyl, thenoyl, and phenacyl groups.

The acylamino group as represented by $R^3$ includes acetylamino, benzoylamino, propanoylamino, furoylamino, N-methylacetylamino, and N-methylbenzoylamino groups.

The carbamoyl group as represented by $R^3$ is generally represented by

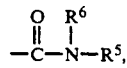

wherein $R^5$ and $R^6$ each have the same meaning as $R^1$, and includes N,N-dimethylcarbamoyl, N-phenylcarbamoyl, and N-dodecylcarbamoyl groups.

The carbamoylamino group as represented by $R^3$ is generally represented by

wherein $R^5$, $R^6$, and $R^7$ each has the same meaning as $R^1$, and includes (N,N-dimethylcarbamoyl)amino, (N-phenylcarbamoyl)amino, and N-methyl-(N'-methylcarbamoyl)amino groups.

The sulfonyl group as represented by $R^3$ is generally represented by $-SO_2-R^5$, wherein $R^5$ has the same meaning as $R^1$, and includes methanesulfonyl, ethanesulfonyl, dodecanesulfonyl, benzenesulfonyl, and tosyl groups.

The sulfonylamino group as represented by $R^3$ is generally represented by

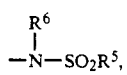

wherein $R^5$ and $R^6$ each have the same meaning as $R^1$, and includes methanesulfonylamino, benzenesulfonylamino, and tosylamino groups.

The sulfamoyl group as represented by $R^3$ is generally represented by

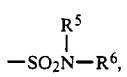

wherein $R^5$ and $R^6$ each have the same meaning as $R^1$, and includes N,N-diethylsulfamoyl, N-dodecylsulfamoyl, and N-phenylsulfamoyl groups.

The sulfamoylamino group as represented by $R^3$ is generally represented by

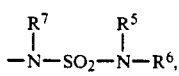

wherein $R^5$, $R^6$, and $R^7$ each have the same meaning as $R^1$, and includes (N,N-diethylsulfamoyl)amino, (N-phenylsulfamoyl)amino, N-methyl-(N'-dodecylsulfamoyl)amino groups.

The alkoxy group as represented by $R^3$ is generally represented by $-O-R^8$, wherein $R^8$ has the same meaning as the aliphatic group used for $R^1$, and includes methoxy, ethoxy, propoxy, butoxy, t-butoxy, 2-ethylhexyloxy, allyloxy, and benzyloxy groups.

The aryloxy group as represented by $R^3$ is generally represented by $-O-R^9$, wherein $R^9$ has the same meaning as the aromatic group used for $R^1$, and includes phenoxy and naphthoxy groups.

The alkoxycarbonyl group as represented by $R^3$ is generally represented by

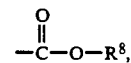

wherein $R^8$ has the same meaning as the aliphatic group used for $R^1$, and includes methoxycarbonyl, ethoxycarbonyl, and hexadecyloxycarbonyl groups.

The aryloxycarbonyl group as represented by $R^3$ is generally represented by

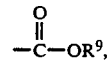

wherein $R^9$ has the same meaning as the aromatic group used for $R^1$, and includes phenoxycarbonyl and naphthoxycarbonyl groups.

The sulfenyl group as represented by $R^3$ is generally represented by $-S-R^5$, wherein $R^5$ has the same meaning as $R^1$, and includes methanesulfenyl, ethanesulfenyl, and benzenesulfenyl groups.

The sulfinyl group as represented by $R^3$ is generally represented by

wherein $R^5$ has the same meaning as $R^1$, and includes methanesulfinyl, ethanesulfinyl, benzenesulfinyl, and p-toluenesulfinyl groups.

The organic group as represented by $R^2$ includes an aliphatic group (the same as in $R^1$ or $R^3$), an aromatic group (the same as in $R^1$ or $R^3$), a heterocyclic group (the same as in $R^1$ or $R^3$), an alkoxy group (the same as that in $R^3$), an aryloxy group (the same as that in $R^3$), or

wherein $R^5$ and $R^6$ each have the same meaning as $R^1$ or are taken together to form a ring.

Each of the above-mentioned groups for $R^1$, $R^2$, $R^3$, $R^5$, $R^6$, $R^7$, $R^8$ and $R^9$ may be substituted with substituent, such as a halogen atom (e.g., fluorine, chlorine, bromine), a straight chain or branched, acyclic or cyclic, saturated or unsaturated, and substituted or unsubstituted aliphatic group (e.g., methyl, propyl, t-butyl, trifluoromethyl, tridecyl, 3-(2,4-di-t-amylphenoxy)propyl, 2-dodecyloxyethyl, 3phenoxypropyl, 2-hexylsulfonylethyl, cyclopentyl, benzyl), an aryl group (e.g., phenyl, 4-t-butylphenyl, 4-tetradecaneamidophenyl), a heterocyclic group (e.g., 2-furyl, 2-thienyl, 2-pyrimidyl, 2-benzothiazolyl), a cyano group, an alkoxy group (e.g., methoxy, ethoxy, 2-methoxyethoxy, 2-dodecyloxyethoxy, 2-methanesulfonylethoxy), an aryloxy group (e.g., phenoxy, 2-methylphenoxy, 4-t-butylphenoxy), a heterocyclic oxy group (e.g., 2-benzimidazolyloxy), an acyloxy group (e.g., acetoxy, hexadecanoyloxy), a carbamoyloxy group (e.g., N-ethylcarbamoyloxy), a silyloxy group (e.g., trimethylsilyloxy), a sulfonyloxy group (e.g., dodecylsulfonyloxy), an acylamino group (e.g., acetamido, benzamido, tetradecaneamido, α-(2,4-di-t-amylphenoxy)-butylamido, 2,4-di-t-amylphenoxyacetamido, α-{4-(4-hydroxyphenylsulfonyl)phenoxy)}decaneamido, isopentadecaneamido), an anilino group (e.g., phenylamino, 2-chloroanilino, 2-chloro-5-tetradecaneamidoanilino, 2-chloro-5-dodecyloxycarbonylanilino, N-acetylanilino, 2-chloro-5-{α-(2-t-butyl-4-hydroxyphenoxy)dodecaneamido}-anilino), a ureido group (e.g., phenylureido, methylureido, N,N-dibutylureido), an imido group (e.g., N-succinimido, 3-benzylhydantoinyl, 4-(2-ethylhexanoylamino)phthalimido), a sulfamoylamino group (e.g., N,N-dipropylsulfamoylamino, N-methyl-N-decylsulfamoylamino), an alkylthio group (e.g., methylthio, octylthio, tetradecylthio, 2-phenoxyethylthio, 3-phenoxypropylthio, 3-(4-t-butylphenoxy)propylthio), an arylthio group (e.g., phenylthio, 2-butoxy-5-t-octylphenylthio, 3-pentadecylphenylthio, 2-carboxyphenylthio, 4-tetradecaneamidophenylthio), a heterocyclic thio group (e.g., 2-benzothiazolylthio), an alkoxycarbonylamino group (e.g., methoxycarbonylamino, tetradecyloxycarbonylamino), an aryloxycarbonylamino group (e.g., phenoxycarbonylamino, 2,4-di-t-butylphenoxycarbonylamino), a sulfonamido group (e.g., methanesulfonamido, hexadecanesulfonamido, benzenesulfonamido, p-toluenesulfonamido, octadecanesulfonamido, 2-methyloxy-5-t-butylbenzenesulfonamido), a carbamoyl group (e.g., N-ethylcarbamoyl, N,N-dibutylcarbamoyl, N-(2-dodecyloxyethyl)carbamoyl, N-methyl-N-dodecylcarbamoyl, N-{3-(2,4-di-t-amylphenoxy)propyl}carbamoyl), an acyl group (e.g., acetyl, (2,4-di-t-amylphenoxy)acetyl, benzoyl), a sulfamoyl group (e.g., N-ethylsulfamoyl, N,N-dipropylsulfamoyl, N-(2-dodecyloxyethyl)sulfamoyl, N-ethyl-N-dodecylsulfamoyl, N,N-diethylsulfamoyl), a sulfonyl group (e.g., methanesulfonyl, octanesulfonyl, benzenesulfonyl, toluenesulfonyl), a sulfinyl group (e.g., octanesulfinyl, dodecylsulfinyl, phenylsulfinyl), an alkoxycarbonyl group (e.g., methoxycarbonyl, butoxycarbonyl, dodecyloxycarbonyl, octadecyloxycarbonyl), and an aryloxycarbonyl group (e.g., phenyloxycarbonyl, 3-pentadecyloxycarbonyl).

The releasable group Z in formula (I) is preferably represented by formula (III) shown below, wherein the coupler residue A is bonded:

$$A-(L_1)_a-P\!-\!(L_2-Q)_b \quad \text{(III)}$$

wherein A represents a coupler residue excluding Z in formula (I); $L_1$ represents a linking group; P represents a basic moiety of a compound having development inhibitory activity which is bonded to the coupling position of the coupler group A directly (when a=0) or via $L_1$ (when a=1); $L_2$ represents a linking group containing a chemical bond which is broken in a developing solution; Q represents a group which is bonded to P via $L_2$ to enable P to manifest a development inhibitory effect; a represents 0 or 1; and b represents 1 or 2; and when b is 2, $-L_2-Q$ may be the same or different.

The compound of formula (I), after coupling with an oxidation product of a color developing agent, releases $^\theta P-(L_2-Q)_b$ or $^\theta L_1-P-(L_2-Q)_b$. $L_1$ in the latter is immediately removed to produce $^\theta P-(L_2-Q)_b$. $^\theta P-(L_2-Q)_b$ diffuses through a light-sensitive layer while manifesting its development inhibitory action and partly diffuses into the color developing solution, where it is rapidly decomposed at the chemical bond in $L_2$. That is, P is released from Q, leaving only a compound comprising P having small development inhibitory activity and a water-soluble group bonded thereto in the color developing solution. Thus, the development inhibitory activity of $^\theta P-(L_2-Q)_b$ is substantially lost in the color developing solution.

No development inhibitory compound accumulates in the processing solution, making it feasible not only to repeatedly reuse the processing solution, but also to incorporate a sufficient amount of a DIR coupler into a light-sensitive material.

The basic moiety (P) of the development inhibitor includes a divalent nitrogen-containing heterocyclic group and a divalent nitrogen-containing heterocyclic thio group (e.g., tetrazolylthio, benzothiazolylthio, benzimidazolylthio, thiadiazolylthio, oxadiazolylthio, triazolylthio, imidazolylthio). Specific examples of P are shown below together with $A-(L_1)_a-$ and $-(L_2-Q)_b$ moieties to illustrate the positions for bonding thereto.

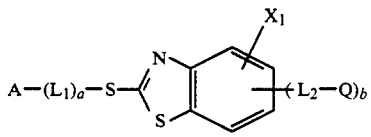

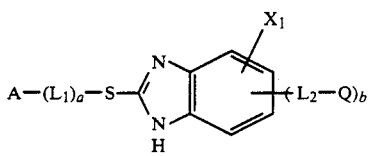

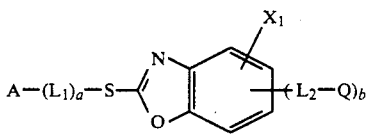

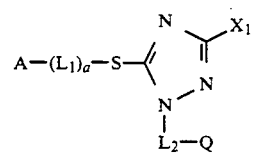

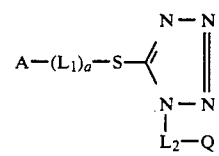

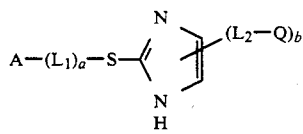

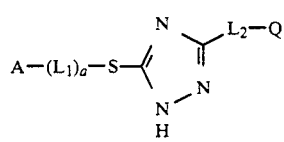

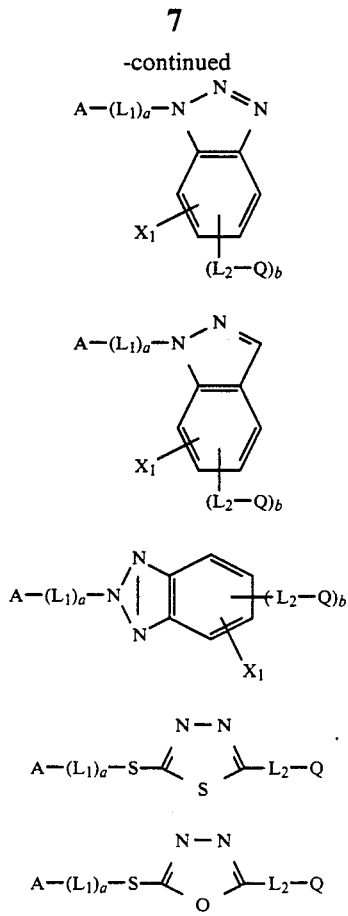

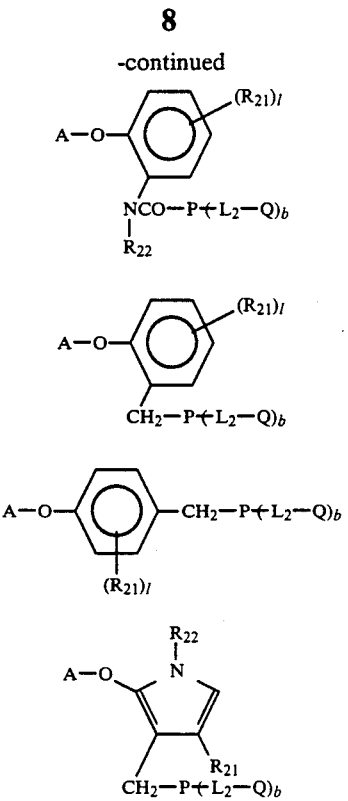

In the above formulae, the substituent represented by $X_1$ is present in the moiety P of formula (III). Suitable examples of the substituent represented by $X_1$ include a hydrogen atom, a halogen atom, an alkyl group, an alkenyl group, an alkaneamido group, an alkeneamido group, an alkoxy group, a sulfonamido group, and an aryl group.

Examples of the group Q in formula (III) include an alkyl group, a cycloalkyl group, an alkenyl group, a cycloalkenyl group, an aryl group, an aralkyl group, and a heterocyclic group.

Examples of the linking group $L_1$ in formula (III) are shown below together with A and P—$(L_2-Q)_b$ moieties.

$$A-OCH_2-P-(L_2-Q)_b$$
(described in U.S. Pat. No. 4,146,396)

$$A-SCH_2-P-(L_2-Q)_b$$

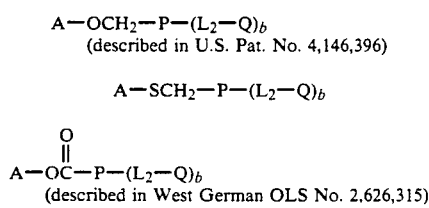

(described in West German OLS No. 2,626,315)

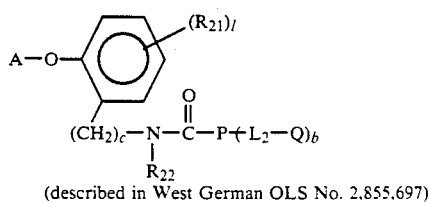

(described in West German OLS No. 2,855,697)

wherein $R_{21}$ represents a hydrogen atom, a halogen atom, an alkyl group, an alkenyl group, an aralkyl group, an alkoxy group, an alkoxycarbonyl group, an anilino group, an acylamino group, a ureido group, a cyano group, a nitro group, a sulfonamido group, a sulfamoyl group, a carbamoyl group, an aryl group, a carboxyl group, a sulfo group, a cycloalkyl group, an alkanesulfonyl group, an arylsulfonyl group, or an acyl group; $R_{22}$ represents a hydrogen atom, an alkyl group, an alkenyl group, an aralkyl group, a cycloalkyl group, or an aryl group; a represents 0, 1 or 2; and b and l represents 1 or 2; and when l is 2, two $R_{21}$ groups may be taken together to form a condensed ring.

The releasable group released from the above illustrated DIR couplers of formula (III) when a is 1 on reaction with an oxidation product of a developing agent, immediately decomposes to release a development inhibitor $P^\theta-(L_2-Q)_b$. Therefore, these DIR couplers have the same effects as those having no linking group $L_1(a=0)$.

The linking group $L_2$ in formula (III) contains a chemical bond which is broken by the action of a nucleophilic reagent in a color developing solution (e.g., a hydroxyl ion and hydroxylamine) to produce the effects of the present invention. Examples of such a chemical bond are shown below together with the mode of their reaction with a hydroxyl ion.

| Chemical Bond in $L_2$ | Reaction with $^\theta OH$ |
|---|---|
| —COO— | —COOH + HO— |
| H<br>—NCOO— | —NH$_2$ + HO— |
| —SO$_2$O— | —SO$_3$H + HO— |
| —OCH$_2$CH$_2$SO$_2$— | —OH + CH$_2$=CHSO$_2$— |

-continued

| Chemical Bond in $L_2$ | Reaction with $^\theta OH$ |
|---|---|
| $-OCO-$<br>$\|$<br>$O$ | $-OH + HO-$ |
| $-NHCCO-$<br>$\|\|\ \|\|$<br>$OO$ | $-NH_2 + HO-$ |

The chemical bonds shown above are bonded at one end thereof to P directly or via an alkylene group and/or a phenylene group and to Q at the other end. Where they are bonded to P via an alkylene or phenylene group, the alkylene or phenylene group may contain therein an ether linkage, an amido linkage, a carbonyl group, a thioether linkage, a sulfone group, a sulfonamido linkage, a urea linkage, etc.

Examples of preferred linking groups as $L_2$ are shown below together with —P— and —Q for illustrating the positions for bonding thereto.

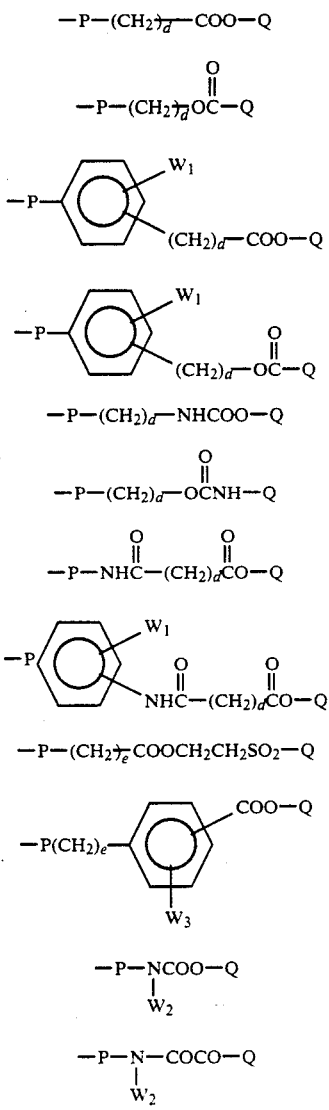

wherein d represents 0 or an integer of from 1 to 10, preferably 0 or an integer of from 1 to 5; $W_1$ represents a hydrogen atom, a halogen atom, an alkyl group hav-ing from 1 to 10 carbon atoms, preferably from 1 to 5 carbon atoms, an alkaneamido group having from 1 to 10 carbon atoms, preferably from 1 to 5 carbon atoms, an alkoxy group having from 1 to 10 carbon atoms, preferably from 1 to 5 carbon atoms, an alkoxycarbonyl group having from 1 to 10 carbon atoms, preferably from 1 to 5 carbon atoms, an aryloxycarbonyl group, an alkanesulfonamido group having from 1 to 10 carbon atoms, preferably from 1 to 5 carbon atoms, an aryl group, a carbamoyl group, an N-alkylcarbamoyl group having from 1 to 10 carbon atoms, preferably from 1 to 5 carbon atoms, in its alkyl moiety, a nitro group, a cyano group, an arylsulfonamido group, a sulfamoyl group, an imido group, etc.; $W_2$ represents a hydrogen atom, an alkyl group having from 1 to 6 carbon atoms, an aryl group, or an alkenyl group; $W_3$ represents a hydrogen atom, a halogen atom, a nitro group, an alkoxy group having from 1 to 6 carbon atoms, or an alkyl group having from 1 to 6 carbon atoms; and e represents 0 or an integer of from 1 to 6.

More specifically, the alkyl or alkenyl group as represented by $X_1$ or Q is a straight chain, branched or cyclic, and substituted or unsubstituted, preferably substituted, alkyl or alkenyl group having from 1 to 10 carbon atoms, preferably from 1 to 5 carbon atoms. Substituents of the alkyl or alkenyl group include a halogen atom, a nitro group, an alkoxy group having from 1 to 4 carbon atoms, an aryloxy group having from 6 to 10 carbon atoms, an alkanesulfonyl group having from 1 to 4 carbon atoms, an arylsulfonyl group having from 6 to 10 carbon atoms, an alkaneamido group having from 1 to 5 carbon atoms, an anilino group, a benzamido group, an alkyl-substituted carbamoyl group having from 1 to 6 carbon atoms in its alkyl moiety, a carbamoyl group, an aryl-substituted carbamoyl group having from 6 to 10 carbon atoms in its aryl moiety, an alkylsulfonamido group having from 1 to 4 carbon atoms, an arylsulfonamido group having from 6 to 10 carbon atoms, an alkylthio group having from 1 to 4 carbon atoms, an arylthio group having from 6 to 10 carbon atoms, a phthalimido group, a succinimido group, an imidazolyl group, a 1,2,4-triazolyl group, a pyrazolyl group, a benzotriazolyl group, a furyl group, a benzothiazolyl group, an alkylamino group having from 1 to 4 carbon atoms, an alkanoyl group having from 1 to 4 carbon atoms, a benzoyl group, an alkanoyloxy group having from 1 to 4 carbon atoms, a benzoyloxy group, a perfluoroalkyl group having from 1 to 4 carbon atoms, a cyano group, a tetrazolyl group, a hydroxyl group, a carboxyl group, a mercapto group, a sulfo group, an amino group, an alkylsulfamoyl group having from 1 to 4 carbon atoms, an arylsulfamoyl group having from 6 to 10 carbon atoms, a morpholino group, an aryl group having from 6 to 10 carbon atoms, a pyrrolidinyl group, a ureido group, a urethane group, an alkoxy-substituted carbonyl group having from 1 to 6 carbon atoms in its alkyl moiety, an aryloxy-substituted carbonyl group having from 6 to 10 carbon atoms in its aryl moiety, an imidazolidinyl group, and an alkylideneamino group having from 1 to 6 carbon atoms.

The alkaneamido group or alkeneamido group as represented by $X_1$ is a straight chain, branched or cyclic and substituted or unsubstituted alkaneamido or alkeneamido group having from 1 to 10 carbon atoms, preferably from 1 to 5 carbon atoms. Substituents of the alkaneamido or alkeneamido group are selected from those set forth above with respect to the alkyl or alkenyl group.

The alkoxy group as represented by $X_1$ is a straight chain, branched or cyclic and substituted or unsubstituted alkoxy group having from 1 to 10 carbon atoms, preferably from 1 to 5 carbon atoms. Substituents of the alkoxy group are selected from those set forth above with respect to the alkyl or alkenyl group.

The sulfonamido group as represented by $X_1$ is preferably a straight chain, branched or cyclic, and substituted or unsubstituted alkanesulfonamido group having from 1 to 10 carbon atoms, preferably from 1 to 6 carbon atoms, or a substituted or unsubstituted arylsulfonamido group having from 6 to 14 carbon atoms, preferably from 6 to 10 carbon atoms. Substituents of the sulfonamido group are selected from those set forth above with respect to the alkyl group or alkenyl group.

The aryl group as represented by Q or $X_1$ is preferably a substituted or unsubstituted phenyl or naphthyl group. Substituents of the phenyl or naphthyl group are selected from those set forth above with respect to the alkyl or alkenyl group and an alkyl group having from 1 to 4 carbon atoms.

The heterocyclic group as represented by Q preferably comprises 5 to 7 members and includes a diazolyl group (e.g., 2-imidazolyl, 4-pyrazolyl), a triazolyl group (e.g., 1,2,4-triazol-3-yl), a thiazolyl group (e.g., 2-benzothiazolyl), an oxazolyl group (e.g., 1,3-oxazol-2-yl), a pyrrolyl group, a pyridyl group, a diazinyl group (e.g., 1,4-diazin-2-yl), a triazinyl group (e.g., 1,2,4-triazin-5-yl), a furyl group, a diazolinyl group (e.g., imidazolin-2-yl), a pyrrolinyl group, and a thienyl group.

The aralkyl group as represented by Q is preferably a straight chain, branched or cyclic and substituted or unsubstituted alkyl group having from 1 to 10 carbon atoms, preferably from 1 to 5 carbon atoms. substituents of the aralkyl group are selected rom those set forth above with respect to the alkyl or alkenyl group, and preferably a phenyl group or a naphthyl group.

Of the couplers represented by formula (III), those represented by formulae (IV) through (X) shown below are preferred in view of the high development inhibitory activity of the released development inhibitor.

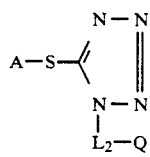  (IV)

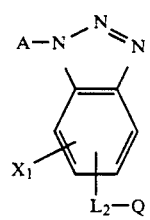  (V)

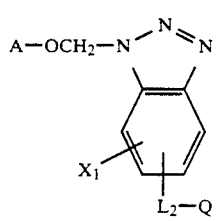  (VI)

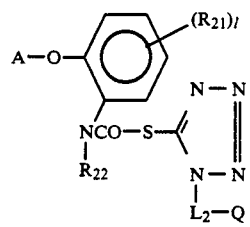  (VII)

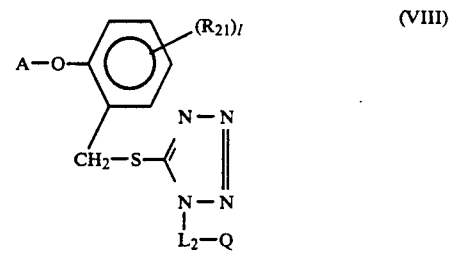  (VIII)

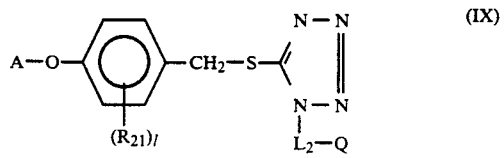  (IX)

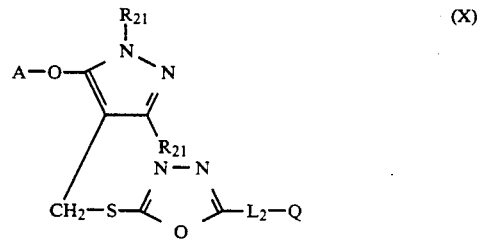  (X)

wherein A, $X_1$, $R_{21}$, $R_{22}$, l, $L_2$, and Q are as defined above.

More preferred of the couplers of formula (III) are those represented by formula (XI):

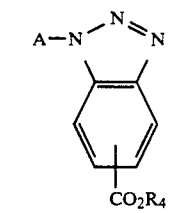  (XI)

wherein A is as above; and $R^4$ represents an aliphatic group having from 1 to 4 carbon atoms or a pyridyl group.

That is, it is more preferable for Z in formula (I) to be represented by formula (II):

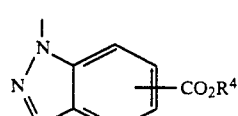  (II)

wherein $R^4$ represents an aliphatic group having from 1 to 4 carbon atoms or a pyridyl group.

In formulas (II) and (XI), the aliphatic group as represented by $R^4$ is a straight chain or branched and substituted or unsubstituted aliphatic group having from 1 to 4 carbon atoms, preferably from 1 to 3 carbon atoms.

The pyridyl group as represented by $R^4$ is a substituted or unsubstituted 2-, 3-, or 4-pyridyl group.

The aliphatic group represented by $R^4$ is preferably a substituted aliphatic group. Suitable substituents of the aliphatic group include an alkoxycarbonyl group having from 2 to 6 carbon atoms (e.g., methoxycarbonyl, propoxycarbonyl, butoxycarbonyl, isobutoxycarbonyl, isopropoxycarbonyl, pentyloxycarbonyl, isopentyloxycarbonyl, 2-methoxyethoxycarbonyl), a carbamoyl group having from 1 to 7 carbon atoms (e.g., N,N-diethylcarbamoyl, N-methyl-N-ethylcarbamoyl, N-hexylcarbamoyl, N-isoamylcarbamoyl, pyrrolidinocarbonyl, piperidinocarbonyl), a halogen atom (e.g., a chlorine atom, a fluorine atom, a bromine atom), a nitro group, a cyano group, an alkoxy group having from 1 to 4 carbon atoms (e.g., methoxy, ethoxy, methoxyethoxy), a sulfamoyl group having up to 6 carbon atoms (e.g., N,N-diethylsulfamoyl, N-hexylsulfamoyl, N-isoamylsulfamoyl), an aryloxy group having from 6 to 10 carbon atoms (e.g., 4-chlorophenoxy, 2,4-dichlorophenyl, 4-cyanophenoxy)), an acyl group having from 2 to 7 carbon atoms (e.g., acetyl, benzoyl), a sulfonyl group having from 1 to 10 carbon atoms .(e.g., methanesulfonyl, butanesulfonyl, benzenesulfonyl, p-toluenesulfonyl), a heterocyclic group (e.g., 2-pyridyl, 3-pyridyl), and a phosphoryl group having from 2 to 5 carbon atoms (e.g., O,O-diethylphosphoryl). Alkoxycarbonyl and carbamoyl groups are preferred from among these substituents.

Suitable substituents for the pyridyl group as represented by $R^4$ include the groups set forth above as substituents for the aliphatic group and, in addition, an aliphatic group having from 1 to 6 carbon atoms (e.g., methyl, ethyl).

Specific examples of $R^4$ include $-CH_2COOC_3H_7(n)$, $-CH_2COOC_4H_9(n)$, $-CH_2COOC_3H_7(i)$, $-CH_2COOC_4H_9(i)$, -continued $-CH_2COOC_5H_{11}(n)$, $-CH_2COOC_5H_{11}(i)$, $-CH_2COOC_5H_{11}(t)$, $-CH_2CH_2COOC_3H_7(n)$, $-CH_2CH_2COOC_3H_7(i)$, $-CH_2CH_2CH_2COOCH_3$, $-CH_2COOCHCH_2CH_3$,
$\qquad\qquad\qquad\qquad\qquad\qquad\quad\ |$
$\qquad\qquad\qquad\qquad\qquad\qquad\ CH_3$ $-CH_2CHCOOC_3H_7(n)$, $-CH_2CON\begin{matrix}C_2H_5\\ CH_3\end{matrix}$
$\quad\ |$
$\ CH_3$ $-CH_2CON\bigcirc$, $-CH_2CON\bigcirc$, $-CH_2CH_2CON\bigcirc$, $-CH_2CONHC_4H_9(n)$, $-CH_2CONHC_5H_{11}(n)$, $-CH_2CONHC_6H_{13}(n)$, $-CH_2CONHC_4H_9(i)$, $-CH_2CHCl_2$, $-CH_2CF_3$, $-CH_2CF_2CF_3$, $-CH_2CF_2CF_3$, $-CH(CH_2Cl)_2$, $-C_3H_7$, $-C_4H_9$, $-CH_2CH_2OC_2H_5$, $CH_2SO_2N(C_2H_5)_2$, $-CH_2CHCO_2CH_3$,
$\qquad\qquad\qquad\qquad\qquad\qquad\qquad\qquad\quad |$
$\qquad\qquad\qquad\qquad\qquad\qquad\qquad\quad OCH_3$ $-CH_2-\text{pyridyl}$, $\text{pyridyl-CH}_3$, $\text{pyridyl-CH}_3$, $-CH_2CH_2NO_2$, and $-CH_2CH-CH_3$.
$\qquad\qquad\qquad\qquad\qquad\qquad\ |$
$\qquad\qquad\qquad\qquad\qquad\ CN$ Specific examples of DIR couplers which can be used in the present invention are shown below for illustration purposes only and should not be construed as limiting the present invention.

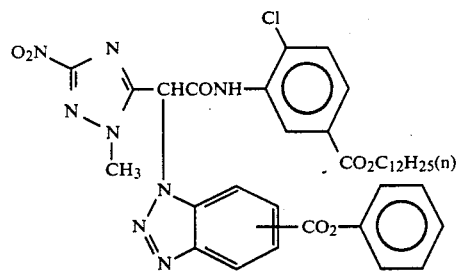

(1)

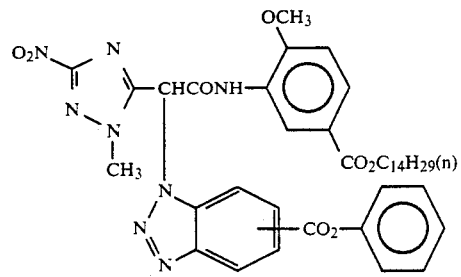

(2)

-continued
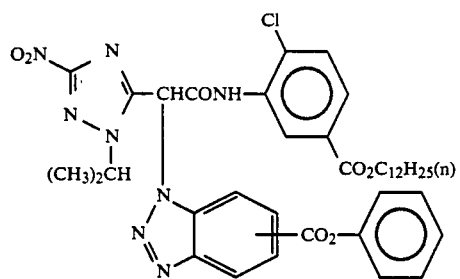
(3)
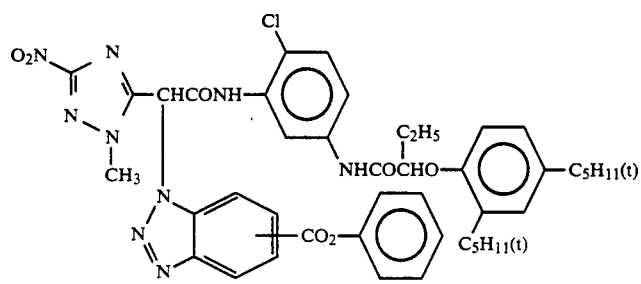
(4)
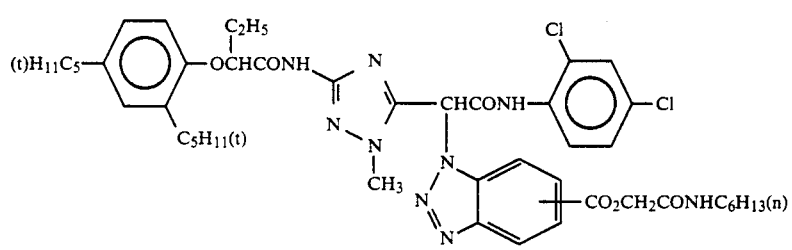
(5)
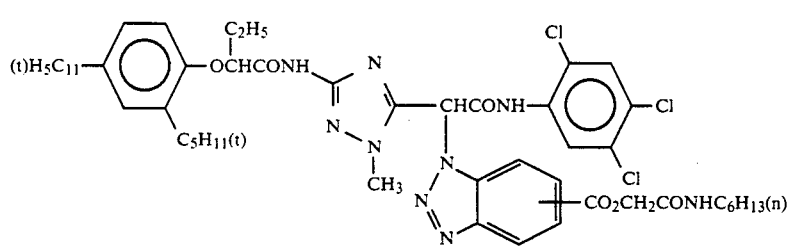
(6)
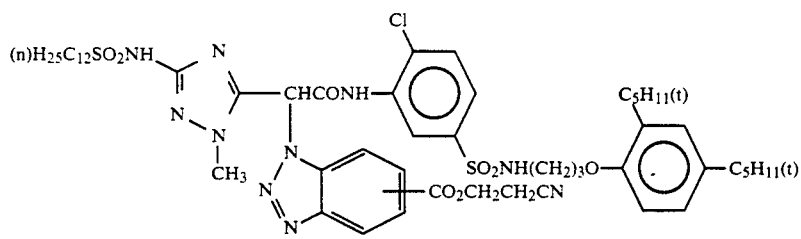
(7)
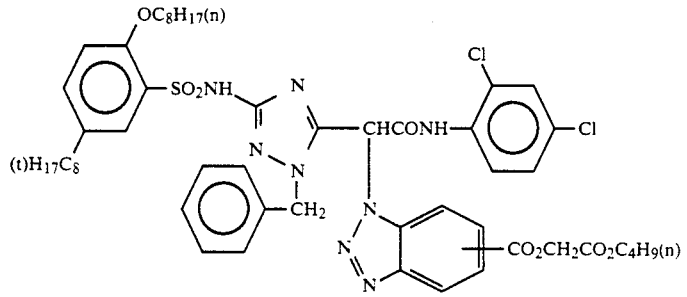
(8)

-continued
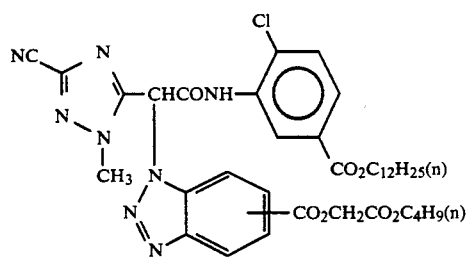 (9)
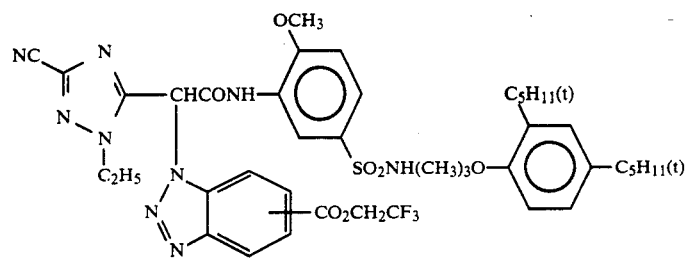 (10)
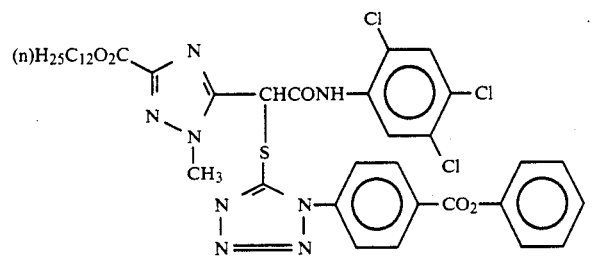 (11)
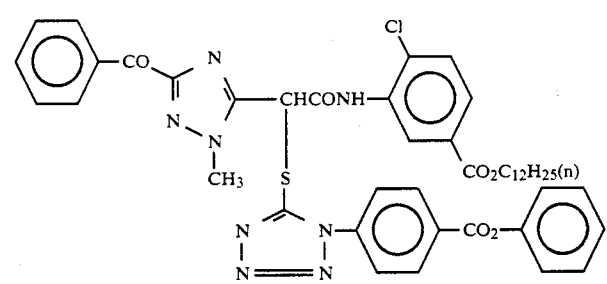 (12)
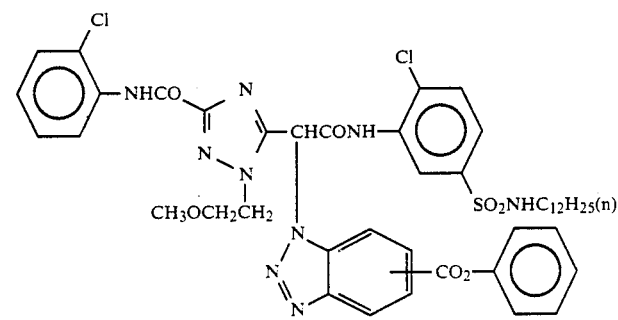 (13)

-continued
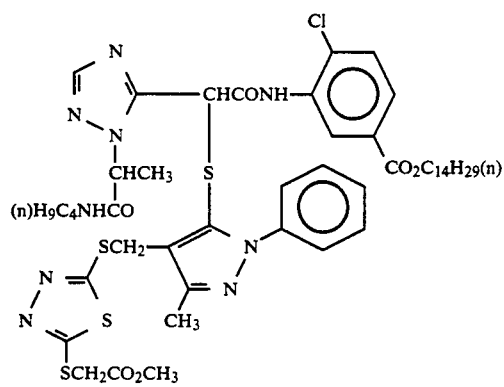 (14)
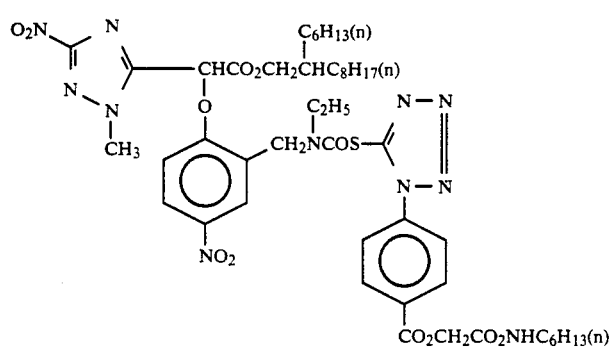 (15)
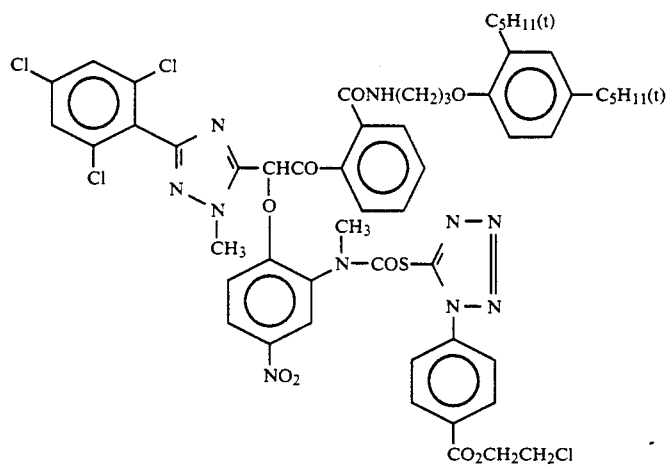 (16)
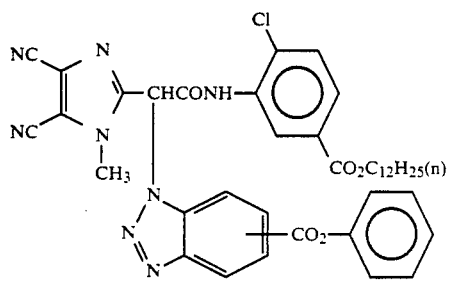 (17)

-continued
(18)
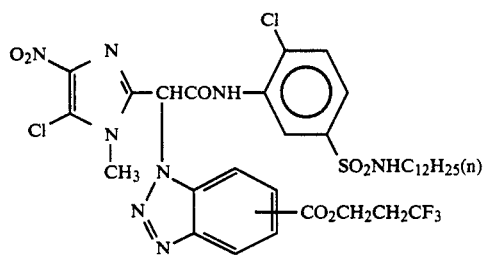
(19)
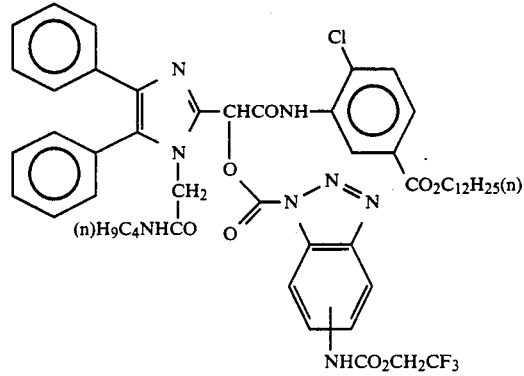
(20)
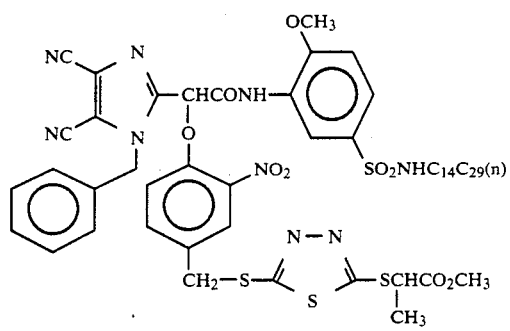
(21)
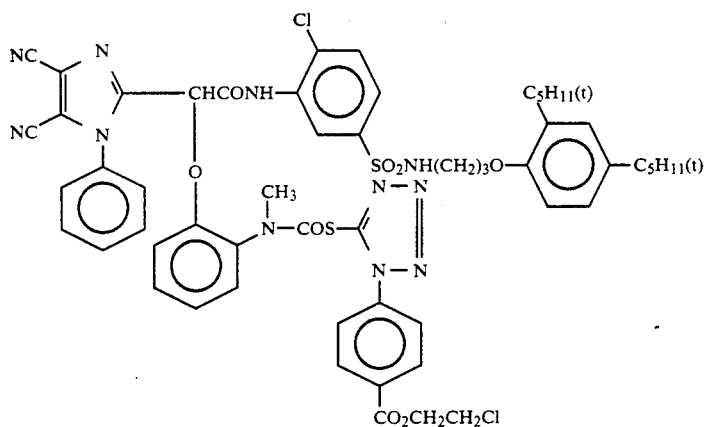
(22)
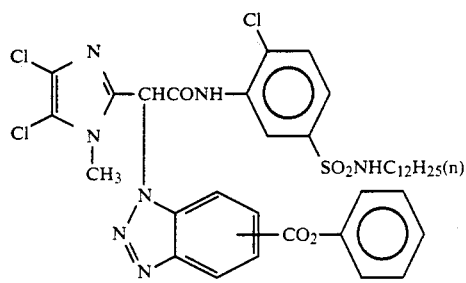

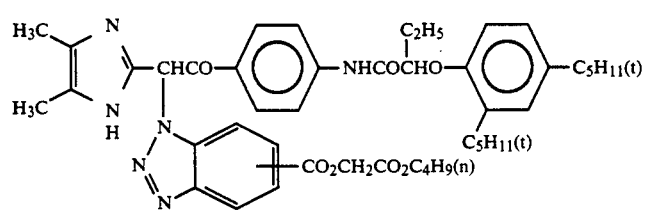
(23)
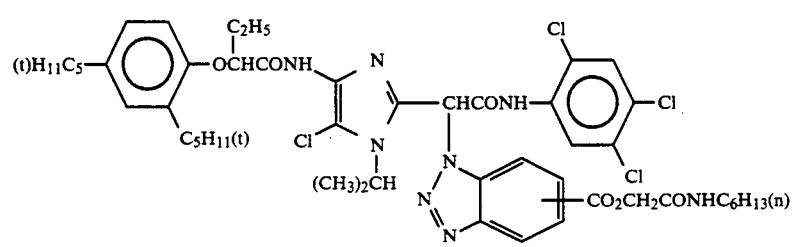
(24)
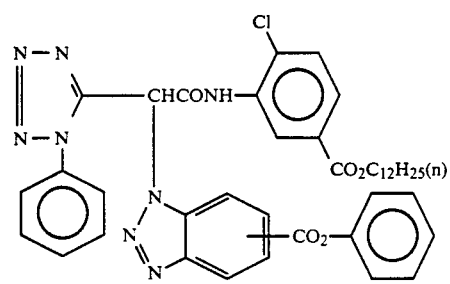
(25)
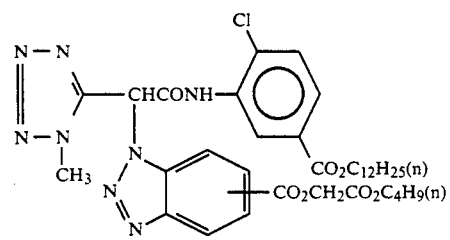
(26)
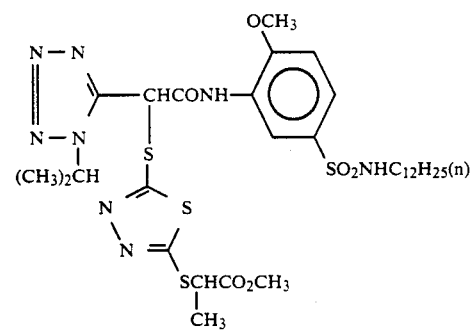
(27)
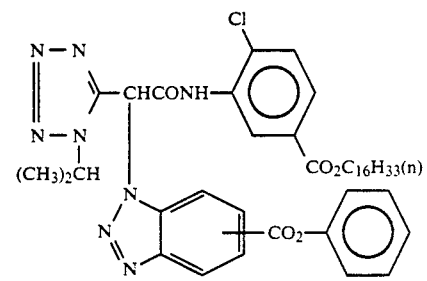
(28)

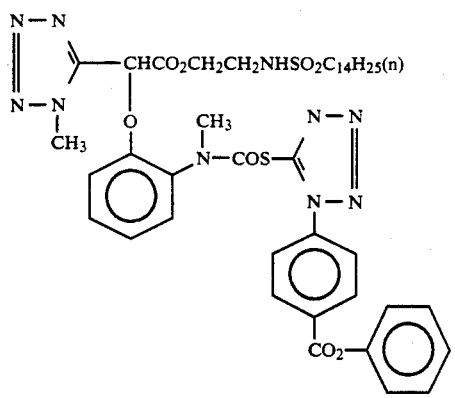
(29)
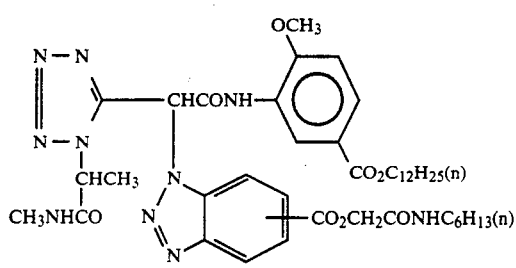
(30)
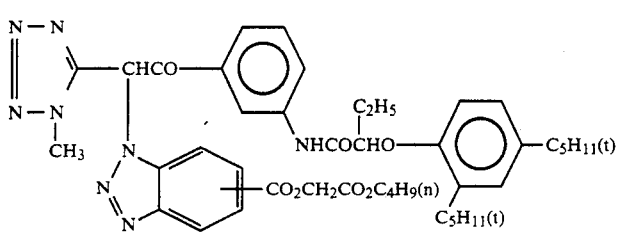
(31)
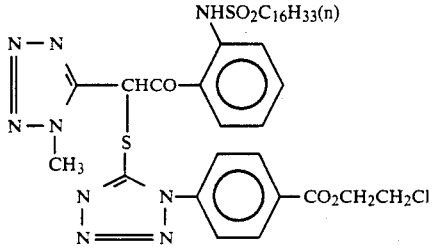
(32)
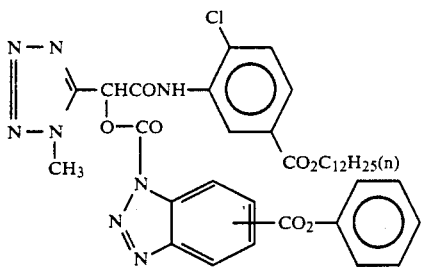
(33)
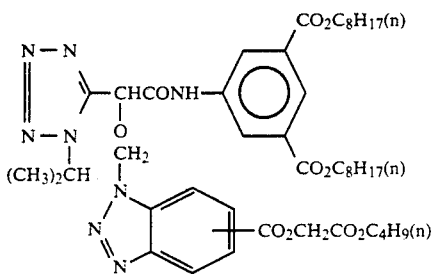
(34)

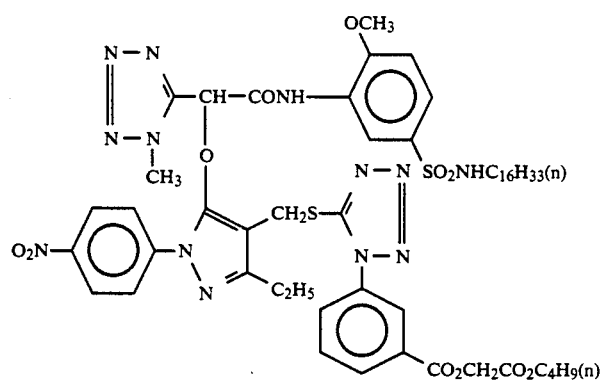
(35)
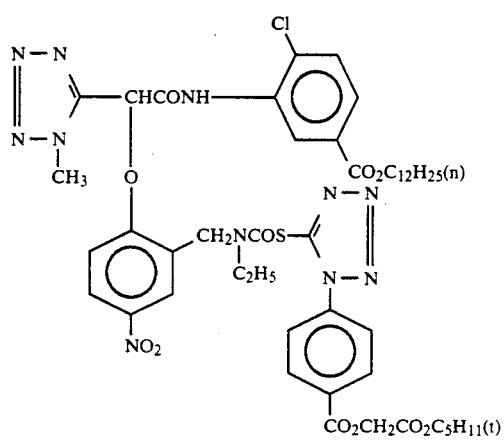
(36)
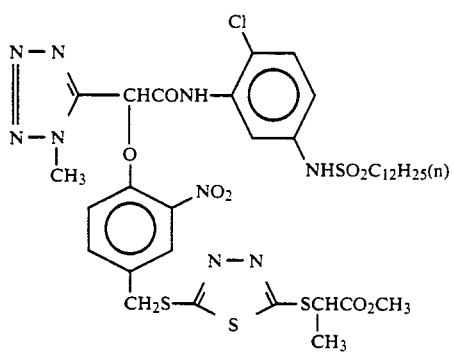
(37)
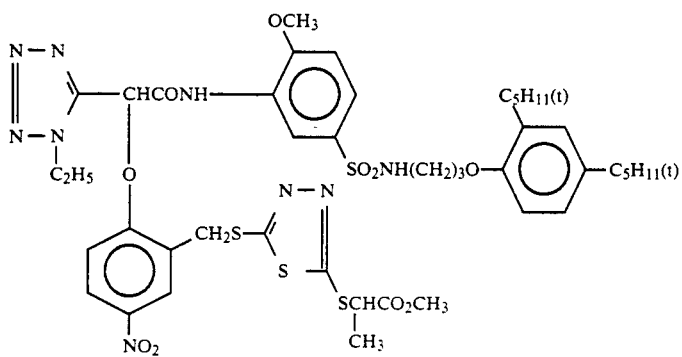
(38)

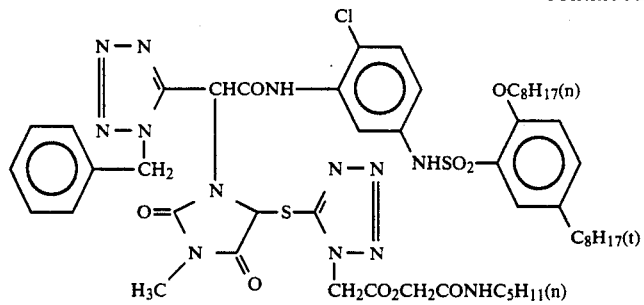

(39)

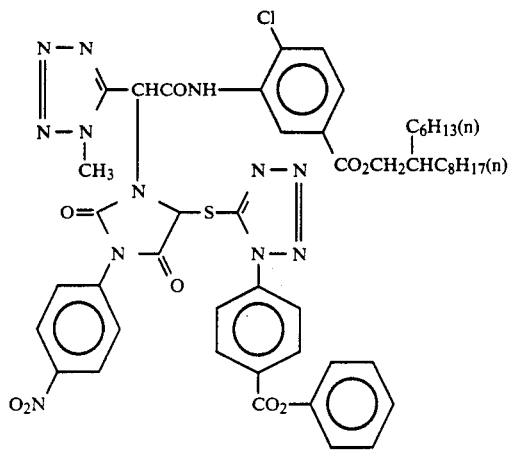

(40)

These compounds can easily be synthesized, for example, by halogenating an active methylene group of a compound represented by formula (XII):

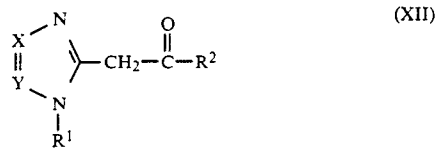

(XII)

wherein X, Y, $R^1$, and $R^2$ are as defined above, in a conventional and reacting the product with ZH, wherein Z is as defined above, in the presence of a base. The compounds of formula (I) wherein Z is bonded via a sulfur atom can also be synthesized by reacting the compound of formula (XII) with a sulfenyl chloride and ZCl obtained by reacting ZH with chlorine gas or sulfuryl chloride.

Synthesis examples of typical compounds according to the present invention are set forth below. Other compounds of the present invention can be synthesized similarly.

SYNTHESIS EXAMPLE 1

Synthesis of Compound (1)

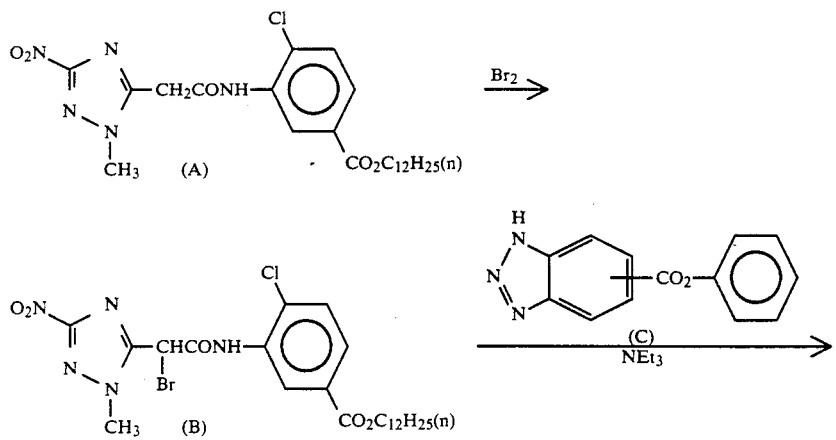

-continued

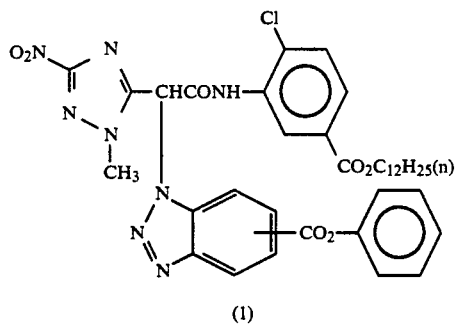

(1)

5.0 g of compound (A) was added to 30 ml of methylene chloride, and 1.65 g of bromine was added to the solution dropwise for 10 minutes under ice-water cool-

SYNTHESIS EXAMPLE 2

Synthesis of Compound (6)

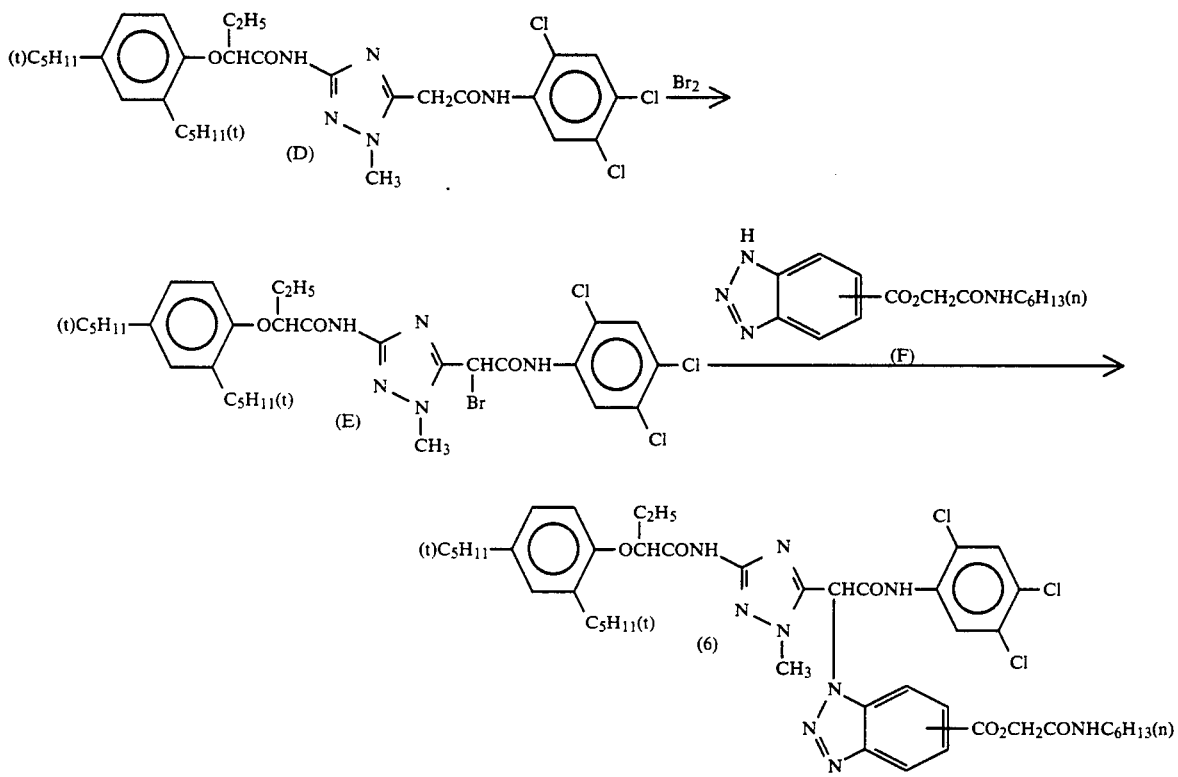

ing. After the reaction, a saturated sodium carbonate aqueous solution was added thereto for liquid-liquid separation three times. After neutralization, the methylene chloride layer was dried over magnesium sulfate. The desiccant was removed by filtration, and the filtrate was added dropwise to a solution of 3.42 g of compound (C) and 1.45 g of triethylamine in 20 ml of dimethylformamide. After the reaction, the reaction mixture was extracted with ethyl acetate. The organic layer was neutralized with diluted hydrochloric acid, washed with water, and dried over magnesium sulfate. The desiccant as removed by filtration, and the solvent was removed by distillation under reduced pressure. The resulting crude product was purified by silica gel column chromatography and then recrystallized from methanol, followed by drying to obtain 3.50 g (65.6% yield) of Compound (1).

5.0 g of Compound (D) was dissolved in 30 ml of methylene chloride, and 1.26 g of bromine was added to the solution dropwise over 10 minutes under cooling with ice-water. After the reaction, a saturated sodium carbonate aqueous solution was added thereto for liquid-liquid separation three times. After neutralization, the methylene chloride layer was dried over magnesium sulfate. The desiccant was removed by filtration, and the filtrate was added dropwise to a solution of 4.78 g of compound (F) and 1.60 g of triethylamine in 20 ml of dimethylformamide. After the reaction, the reaction mixture was extracted with ethyl acetate. The organic layer was neutralized with diluted hydrochloric acid, washed with water, and dried over magnesium sulfate. The desiccant as removed by filtration, and the solvent was removed by distillation under reduced pressure. The resulting crude product was purified by silica gel column chromatography and then recrystallized from an n-hexane-ethyl acetate mixed solvent, followed by drying to obtain 4.06 g (55.0% yield) of Compound (6).

SYNTHESIS EXAMPLE 3

Synthesis of Compound (17)

10.4 g of compound (C) and 4.39 g of triethylamine in 20 ml of dimethylformamide. After the reaction, the reaction mixture was extracted with ethyl acetate. The organic layer was neutralized with diluted hydrochloric acid, washed with water, and dried over magnesium

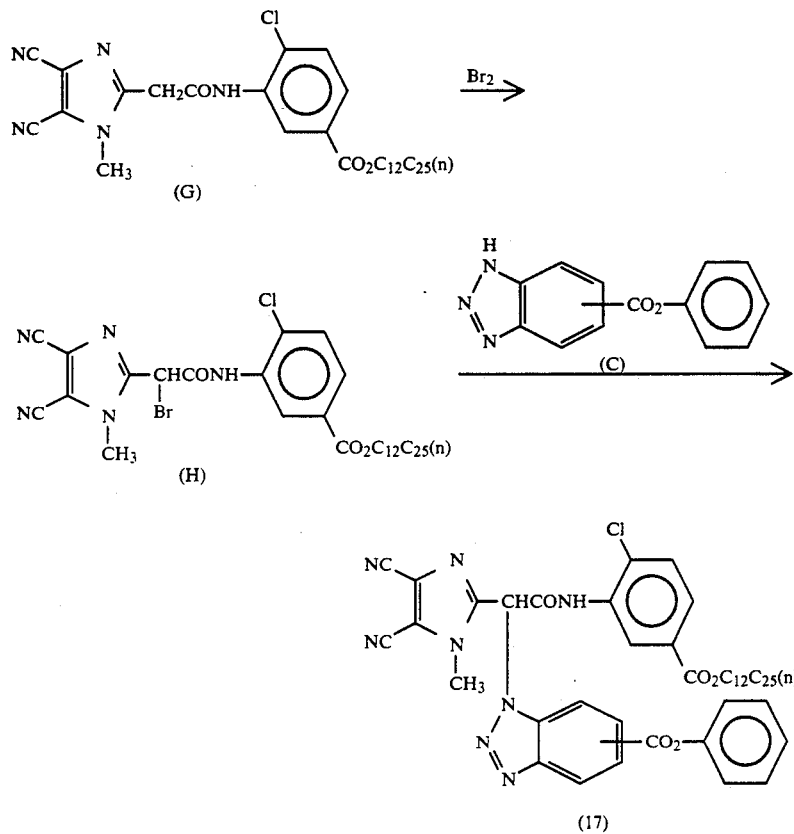

11.0 g of Compound (G) was dissolved in 50 ml of methylene chloride, and 3.46 g of bromine was added to the solution dropwise over 20 minutes while cooling with ice-water. After the reaction, a saturated aqueous solution of sodium carbonate was added thereto for liquid-liquid separation three times. After neutralization, the methylene chloride layer was dried over magnesium sulfate. The desiccant was removed by filtration, and the filtrate was added dropwise to a solution of sulfate. The desiccant as removed by filtration, and the solvent was removed by distillation under reduced pressure. The resulting crude product was purified by silica gel column chromatography and then recrystallized from methanol-ethyl acetate mixed solvent, followed by drying to obtain 7.86 g (48.3% yield) of Compound (17).

SYNTHESIS EXAMPLE 4

Synthesis of Compound (23)

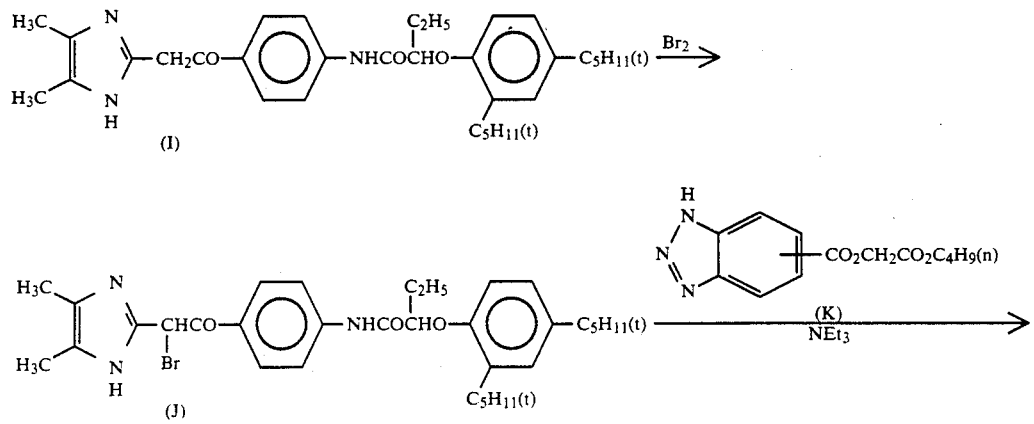

-continued

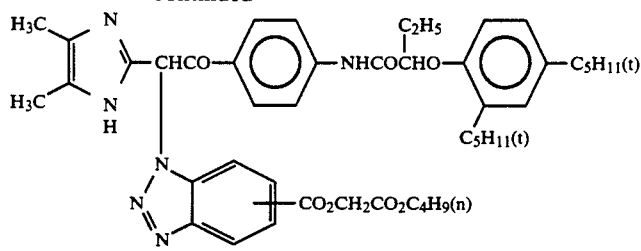

5.0 g of Compound (I) was dissolved in 30 ml of methylene chloride, and 1.58 g of bromine was added to the solution dropwise over 10 minutes while cooling with ice-water. After the reaction, a saturated aqueous solution of sodium carbonate was added thereto for liquid-liquid separation three times. After neutralization, the methylene chloride layer was dried over magnesium sulfate. The desiccant was removed by filtration, and the filtrate was added dropwise to a solution of 5.21 g of compound (K) and 1.90 g of triethylamine in 20 ml of dimethylformamide. After the reaction, the reaction mixture was extracted with ethyl acetate. The organic layer was neutralized with diluted hydrochloric acid, washed with water, and dried over magnesium sulfate. The desiccant as removed by filtration, and the solvent was removed by distillation under reduced pressure. The resulting crude product was purified by silica gel column chromatography and then recrystallized from acetonitrile, followed by drying to obtain 5.23 g (64.8% yield) of Compound (23).

SYNTHESIS EXAMPLE 5

Synthesis of Compound (25)

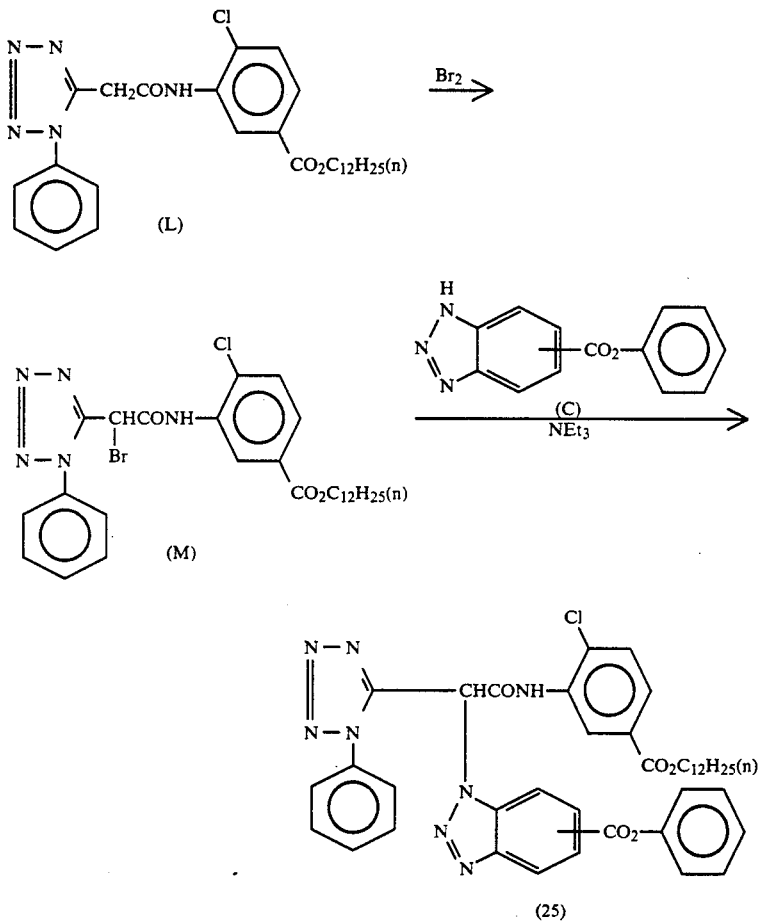

5.00 g of Compound (L) was dissolved in 30 ml of methylene chloride, and 1.59 g of bromine was added to the solution dropwise over 10 minutes while cooling with ice-water. After the reaction, a saturated aqueous solution of sodium carbonate was added thereto for liquid-liquid separation three times. After neutralization, the methylene chloride layer was dried over magnesium sulfate. The desiccant was removed by filtration, and the filtrate was added dropwise to a solution of 4.55 g of compound (C) and 1.92 g of triethylamine in 20 ml of dimethylformamide. After the reaction, the reaction mixture was extracted with ethyl acetate. The organic layer was neutralized with diluted hydrochloric acid, washed with water, and dried over magnesium sulfate. The desiccant as removed by filtration, and the solvent was removed by distillation under reduced pressure. The resulting crude product was purified by silica gel column chromatography and then recrystallized from methanol, followed by drying to obtain 4.53 g (62.4% yield) of Compound (25).

The compound of formula (I) is preferably used in an amount of from $1 \times 10^{-7}$ to 0.5 mol, more preferably from $1 \times 10^{-6}$ to $1 \times 10^{-1}$ mol, per mol of silver present in the layer where it is added or a layer adjacent thereto.

The compound of formula (I) may be used in a layer either individually or in combination with at least one known coupler. When combined, the molar ratio of the compound of formula (I) to the other dye image-forming couplers is in a range of from 0.1/99.9 to 90/10, preferably from 1/99 to 50/50.

Light-sensitive materials according to the present invention comprise a support having thereon at least one of blue-sensitive, green-sensitive, and red-sensitive silver halide emulsion layers. The number and order of silver halide emulsion layers and light-insensitive layers are not particularly limited. A typical material comprises a support having thereon at least one light-sensitive layer (hereinafter referred to as a unit light-sensitive layer) composed of two or more silver halide emulsion layers which have substantially the same color sensitivity to blue light, green light or red light but which are different in photosensitivity. Multi-layer silver halide color photographic materials generally comprise a support having thereon a red-sensitive unit layer, a green-sensitive unit layer, and a blue-sensitive unit layer in such an order. Depending on the end use, the above order of layers may be altered, or two layers having the same color sensitivity may have therebetween a layer having different color sensitivity.

A light-insensitive layer, including various intermediate layers, may be provided between, above, or below these silver halide light-sensitive layers.

Such intermediate layers may contain couplers, DIR compounds, etc., as described in JP-A-61-43748, JP-A-59-113438, JP-A-59-113440, JP-A-61-20037, and JP-A-61-20038, and may also contain color mixing inhibitors as usual.

Each unit light-sensitive layer preferably has a two-layer structure composed of a high sensitive emulsion layer and a low sensitive emulsion layer as described in West German Patent 1,121,470 and British Patent 923,045. The two layers of each unit light-sensitive layer are generally provided in a descending order of photosensitivity in the direction toward the support. Between the two silver halide emulsion layers, a light-insensitive layer may be provided. It is also possible to provide a low sensitive emulsion layer on the side farther from the support and a high sensitive emulsion layer on the side closer to the support, as described in JP-A-57-112751, JP-A-62-200350, JP-A-62-206541, and JP-A-62-206543.

Specific examples of practical layer orders include an order of low sensitive blue-sensitive layer (BL)/high sensitive blue-sensitive layer (BH)/high sensitive green-sensitive layer (GH)/low sensitive green-sensitive layer (GL)/high sensitive red-sensitive layer (RH)/low sensitive red-sensitive layer (RL)/support, an order of BH/BL/GL/GH/RH/RL/support, and an order of BH/BL/GH/GL/RL/RH/support.

A layer order of blue-sensitive layer/GH/RH/GL/RL/support as described in JP-B-55-34932 (the term "JP-B" as used herein means an examined published Japanese patent application") and a layer order of blue-sensitive layer/GL/RL/GH/RH/support as described in JP-A-56-25738 and JP-A-62-63936 can also be used.

Further, a unit light-sensitive layer may be composed of three layers whose photosensitivity differs in a descending order in the direction toward the support (i.e., the most sensitive silver halide emulsion layer as the upper layer, a middle sensitive silver halide emulsion layer as an intermediate layer, and the least sensitive silver halide emulsion layer as the lower layer) as described in JP-B-49-15495. Three layers of different sensitivity in each unit layer may be arranged in the order of middle sensitive emulsion layer/high sensitive emulsion layer/low sensitive emulsion layer from the side farther from a support, as described in JP-A-59-202464.

Furthermore, an order of high sensitive emulsion layer/low sensitive emulsion layer/middle sensitive emulsion layer or an order of low sensitive emulsion layer/middle sensitive emulsion layer/high sensitive emulsion layer can also be used.

In the case where a unit layer is composed of 4 or more layers, the layer arrangement can be altered similarly.

As mentioned above, a layer structure or arrangement of light-sensitive materials can be appropriately chosen according to the end use.

Silver halide which can be used in the photographic emulsion layers is preferably silver iodobromide, silver iodochloride or silver iodochlorobromide, each having a silver iodide content of at most about 30 mol %, more preferably silver iodobromide or silver iodochlorobromide having a silver iodide content of from about 2 mol % to about 10 mol %.

Silver halide grains of the photographic emulsions may have a regular crystal form, such as a cubic form, an octahedral form, or a tetradecahedral form; an irregular crystal form, such as a spherical form or a plate form; a crystal form having a crystal defect, such as a twinning plane; or a composite crystal form thereof.

Silver halide grains may have a wide variety of grain sizes, ranging from fine grains of about 0.2 μm or smaller to large grains having a projected area diameter reaching about 10 μm. The silver halide emulsion may be either a mono-dispersed emulsion or a poly-dispersed emulsion.

Silver halide photographic emulsions which may be used in the present invention can be prepared by the processes described, e.g., in *Research Disclosure* (hereinafter abbreviated as RD), No. 17643 (Dec., 1978), pp. 22–23, "I. Emulsion Preparation and Types", ibid, No. 18716 (Nov., 1979), p. 648, ibid, No. 307105 (Nov., 1989), pp. 863–865, P. Glafkides, *Chemie et Physique Photographique* (Paul Montel, 1967), G. F. Duffin, *Photographic Emulsion Chemistry* (Focal Press, 1966), and V. L. Zelikman et al., *Making and Coating Photographic Emulsion* (Focal Press, 1964).

Mono-dispersed emulsions described in U.S. Pat. Nos. 3,574,628 and 3,655,394 and British Patent 1,413,748 may be preferably used as well.

Tabular grains having an aspect ratio of about 3 or more are also useful. Such tabular grains can easily be prepared by the processes described, e.g., in Gutoff, *Photographic Science and Engineering*, Vol. 14, pp.

248-257 (1970), U.S. Pat. Nos. 4,434,226, 4,414,310, 4,433,048, and 4,439,520, and British Patent 2,112,157.

The silver halide grains may be homogeneous grains having a uniform crystal structure throughout the individual grains or heterogeneous grains, including those in which the inside and the outer shell have different halogen compositions, those in which the halogen composition differs among layers, and those having fused thereto silver halide of different halogen composition through epitaxy. Silver halide grains fused with compounds other than silver halides, e.g., silver rhodanide or lead oxide, may also be used. A mixture comprising grains of various crystal forms can also be used.

The photographic emulsions may be either the surface latent image type, which forms a latent image predominantly on the surface of grains, or the internal latent image type, which forms a latent image predominantly in the inside of the grains, but they should be of the negative type. Internal latent image type emulsions may be of the core/shell type as described in JP-A-63-264740. The core/shell type internal latent image type emulsions can be prepared by the process described in JP-A-59-133542. The thickness of the shell of this type of emulsion preferably ranges from 3 to 40 nm, particularly from 5 to 20 nm, a though the thickness may vary depending on the developing processing.

Silver halide emulsions are usually subjected to physical ripening, chemical ripening, and spectral sensitization. Additives which can be used in these steps are described in RD, Nos. 17643, 18716, and 307105, as hereinafter listed.

In the light-sensitive material of the present invention, a mixture of two or more light-sensitive emulsions differing in at least one of characteristics including grain size, grain size distribution, halogen composition, crystal form, and sensitivity can be used in the same layer.

Surface-fogged silver halide grains as described in U.S. Pat. No. 4,082,553, inside-fogged silver halide grains as described in U.S. Pat. No. 4,626,498 and JP-A-59-214852, and colloidal silver can be preferably used in light-sensitive silver halide emulsion layers and/or substantially light-insensitive hydrophilic colloidal layers. The terminology "inside- or surface-fogged silver halide grains" as used herein means silver halide grains which are evenly (non-imagewise) developable, exposed or unexposed, without distinction. Methods for preparing inside- or surface-fogged silver halide grains are described in U.S. Pat. No. 4,626,498 and JP-A-59-14852.

In the inside-fogged core/shell type silver halide grains, the core and the outer shell may have either the same or different halogen composition.

The inside- or surface-fogged silver halide grains may have any halogen composition selected from silver chloride, silver chlorobromide, silver iodobromide, and silver chloroiodobromide. While these fogged silver halide grains are not particularly limited in grain size, a preferred mean grain size is from 0.01 to 0.75 $\mu$m, particularly from 0.05 to 0.6 $\mu$m. The fogged silver halide grains are not particularly limited in crystal form, either regular or irregular. A polydispersed emulsion can be used, but a mono-dispersed emulsion in which at least 95% of the total weight or number of silver halide grains have a grain size falling within ±40% of a mean grain size is preferred.

In the present invention, light-insensitive silver halide fine grains can be preferably used for the purpose, for example, of trapping disadvantageous substance for development introduced from developing solution. The terminology "light-insensitive silver halide fine grains" as used herein means silver halide fine grains which are not sensitive to light from imagewise exposure for obtaining a color image and are therefore not substantially developed during development processing. It is preferable that the light-insensitive silver halide fine grains are not previously fogged.

The silver halide fine grains have a silver bromide content of from 0 to 100 mol % and may contain, if desired, silver chloride and/or silver iodide, preferably at a silver iodide content of from 0.5 to 10 mol %.

The silver halide fine grains preferably have a mean grain size (an average circle-equivalent diameter of the projected area) of from 0.01 to 0.5 $\mu$m, more preferably from 0.02 to 0.2 $\mu$m.

The silver halide fine grains can be prepared in the same manner as for general light-sensitive silver halide grains. The surface the silver halide fine grains needs to be neither optically sensitized nor spectrally sensitized. It is desirable, however, that a known stabilizer, such as triazole compounds, azaindene compounds, benzothiazolium compounds, mercapto compounds, and zinc compounds, be added before the silver halide fine grains are added to a coating composition. The layer containing the silver halide fine grains preferably contains colloidal silver.

The light-sensitive material of the present invention preferably has a silver coverage of not more than 6.0 g/m$^2$, more preferably not more than 4.5 g/m$^2$.

Known photographic additives which can be used in the present invention are described in RD, Nos. 17643, 18716, and 307105, supra, as shown below.

| Additive | RD 17643 | RD 18716 | RD 307105 |
|---|---|---|---|
| 1. Chemical Sensitizer | p. 23 | p. 648, right column (RC) | p. 866 |
| 2. Sensitivity Increasing Agent | | p. 648, RC | |
| 3. Spectral Sensitizer, Supersensitizer | pp. 23–24 | p. 648, RC to p. 649, RC | pp. 866–868 |
| 4. Brightening Agent | p. 24 | p. 647, RC | p. 868 |
| 5. Antifoggant, Stabilizer | pp. 24–25 | p. 649, RC | pp. 868–870 |
| 6. Light Absorber, Filter Dye, Ultraviolet Absorber | pp. 25–26 | p. 649, RC to P. 650, left column (LC) | p. 873 |
| 7. Stain Inhibitor | p. 25, RC | P. 650, LC to RC | p. 872 |
| 8. Dye Image Stabilizer | p. 25 | p. 650, LC | p. 872 |
| 9. Hardening Agent | p. 26 | p. 651, LC | pp. 874–875 |
| 10. Binder | p. 26 | p. 651, LC | pp. 873–874 |
| 11. Plasticizer, Lubricant | p. 27 | P. 650, RC | p. 876 |
| 12. Coating Aid, Surface Active Agent | pp. 26–27 | p. 650, RC | pp. 875–876 |
| 13. Antistatic Agent | p. 27 | p. 650, RC | pp. 876–877 |
| 14. Matting Agent | | | pp. 878–879 |

In order to prevent deterioration in photographic performance due to formaldehyde gas, a compound capable of reacting with formaldehyde to fix it as described in U.S. Pat. Nos. 4,411,987 and 4,435,503 is preferably added to the light-sensitive materials.

The light-sensitive material of the invention preferably contains the mercapto compound described in U.S. Pat. Nos. 4,740,454 and 4,788,132, JP-A-62-18539, and JP-A-1-283551.

The light-sensitive material preferably contains a compound capable of releasing a fogging agent, a development accelerator, a silver halide solvent, or a precursor thereof regardless of the amount of developed silver produced by development processing, as described in JP-A-1-106052.

The light-sensitive material preferably contains the dye dispersion described in WO 88/04794 and JP-A-1-02912 or the dye described in EP 317,308A, U.S. Patent 4,420,555 and JP-A-1-259358.

Various couplers can be used in the present invention. Specific examples of useful couplers are described in patents cited in RD, No. 17643, VII-C to G, and RD, No. 307105, VII-C to G.

Examples of suitable yellow couplers are described, e.g., in U.S. Pat. Nos. 3,933,501, 4,022,620, 4,326,024, 4,401,752, and 4,248,961, JP-B-58-10739, British Patents 1,425,020 and 1,476,760, U.S. Pat. Nos. 3,973,968, 4,314,023, and 4,511,649, and EP 249,473A.

Examples of suitable magenta couplers include 5-pyrazolone couplers and pyrazoloazole couplers. Examples of particularly preferred magenta couplers are described in U.S. Pat. Nos. 4,310,619 and 4,351,897, European Patent 73,636, U.S. Pat. Nos. 3,061,432 and 3,725,067, RD No. 24220 (Jun., 1984), JP-A-60-33552, RD No. 24230 (Jun., 1984), JP-A-60-43659, JP-A-61-72238, JP-A-60-35730, JP-A-55-118034, JP-A-60-185951, U.S. Pat. Nos. 4,500,630, 4,540,654, and 4,556,630, and WO 8/04795.

Cyan couplers include phenol couplers and naphthol couplers. Examples of suitable couplers are described in U.S. Pat. Nos. 4,052,212, 4,146,396, 4,228,233, 4,296,200, 2,369,929, 2,801,171, 2,772,162, 2,895,826, 3,772,002, 3,758,308, 4,334,011, and 4,327,173, West German Patent Publication No. 3,329,729, EP 121,365A, EP 249,453A, U.S. Pat. Nos. 3,446,622, 4,333,999, 4,775,616, 4,451,559, 4,427,767, 4,690,889, 4,254,212, and 4,296,199, and JP-A-61-42658. Pyrazoloazole type couplers described in JP-A-64-553, JP-A-64-554, JP-A-64-555, and JP-A-64-556 and imidazole type couplers described in U.S. Pat. No. 4,818,672 may also be used.

Typical examples of polymerized dye-forming couplers are described in U.S. Pat. Nos. 3,451,820, 4,080,211, 4,367,282, 4,409,320, and 4,576,910, British Patent 2,102,137, and EP 341,188A.

Examples of suitable couplers which develop a dye having moderate diffusibility are described in U.S. Pat. No. 4,366,237, British Patent 2,125,570, European Patent 96,570, and West German Patent (OLS) No. 3,234,533.

Examples of suitable colored couplers which can be used for correcting unnecessary absorption of a developed dye are described in RD, No. 17643, VII-G, ibid, No. 307105, VII-G, U.S. Patent 4,163,670, JP-B-57-39413, U.S. Pat. Nos. 4,004,929 and 4,138,258 and British Patent 1,146,368. Further, couplers capable of releasing a fluorescent dye upon coupling with which unnecessary absorption of a developed dye is corrected as described in U.S. Pat. No. 4,774,181 and couplers having a dye precursor group as a releasable group which is capable of reacting with a developing agent to form a dye as described in U.S. Pat. No. 4,777,120 are preferably used.

Couplers capable of releasing a photographically useful group on coupling can also be used advantageously. Examples of suitable DIR couplers capable of releasing a development inhibitor, other than those represented by formula (I), are described in patents cited in RD, No. 17643, VII-F, ibid, No. 307105, VII-F, JP-A-57-151944, JP-A-57-154234, JP-A-60-184248, JP-A-63-37346, JP-A-63-37350, and U.S. Pat. Nos. 4,248,962 and 4,782,012.

Examples of suitable couplers which imagewise release a nucleating agent or a development accelerator at the time of development are described in British Patents 2,097,140 and 2,131,188, JP-A-59-157638, and JP-A-59-170840. Compounds capable of releasing a fogging agent, a development accelerator, a silver halide solvent, etc., upon an oxidation-reduction reaction with an oxidation product of a developing agent as described in JP-A-60-107029, JP-A-60-252340, and JP-A-1-44940 are also preferably used.

Additional examples of couplers which can be used in the light-sensitive material of the present invention include competing couplers as described in U.S. Pat. No. 4,130,427; polyequivalent couplers as described in U.S. Pat. Nos. 4,283,472, 4,338,393, and 4,310,618; couplers capable of releasing a DIR redox compound, couplers capable of releasing a DIR coupler, redox compounds capable of releasing a DIR coupler, or redox compounds capable of releasing a DIR redox compound as described in JP-A-60-185950 and JP-A-62-24252; couplers capable of releasing a dye which restores its color after release as described in EP 173,302A and EP 313,308A; couplers capable of releasing a bleaching accelerator as described in RD, Nos. 11449 and 24241 and JP-A-61-201247; couplers capable of releasing a ligand as described in U.S. Pat. No. 4,555,477; couplers capable of releasing a leuco dye as described in JP-A-63-75747; and couplers capable of releasing a fluorescent dye as described in U.S. Patent 4,774,181.

These couplers are introduced into the photographic materials by various known dispersion methods. High-boiling organic solvents which are useful in an oil-in-water dispersion method are described, e.g., in U.S. Pat. No. 2,322,027. Specific examples of the high-boiling organic solvents having a boiling point of 175° C. or higher under atmospheric pressure are phthalic esters (e.g., dibutyl phthalate, dicyclohexyl phthalate, di-2-ethylhexyl phthalate, decyl phthalate, bis(2,4-di-t-amylphenyl) phthalate, bis(2,4-di-t-amylphenyl) isophthalate, bis(1,1-diethylpropyl) phthalate), phosphoric or phosphonic esters (e.g., triphenyl phosphate, tricresyl phosphate, 2-ethylhexyldiphenyl phosphate, tricyclohexyl phosphate, tri-2-ethylhexyl phosphate, tridodecyl phosphate, tributoxyethyl phosphate, trichloropropyl phosphate, di-2-ethylhexylphenyl phosphonate), benzoic acid esters (e.g., 2-ethylhexyl benzoate, dodecyl benzoate, 2-ethylhexyl p-hydroxybenzoate), amides (e.g., N,N-diethyldodecanamide, N,N-diethyllaurylamide, N-tetradecylpyrrolidone), alcohols or phenols (e.g., isostearyl alcohol, 2,4-di-t-amylphenol), aliphatic carboxylic acid esters (e.g., bis(2-ethylhexyl) sebacate, dioctyl azelate, glycerol tributyrate, isostearyl lactate, trioctyl citrate), aniline derivatives (e.g., N,N-dibutyl-2-butoxy-5-t-octylaniline), and hydrocarbons (e.g., paraffin, dodecylbenzene, diisopropylnaphthalane). Organic solvents having a boiling point of not lower than about 30° C., and preferably from 50° C. to about 160° C. may be used in combination as an auxiliary solvent. Typical examples of such are ethyl acetate, butyl acetate, ethyl propionate, methyl ethyl ketone, cyclohexanone, 2-ethoxyethyl acetate, and dimethylformamide.

With respect to a latex dispersion method, the steps involved, the effects, and specific examples of loadable latices are described in U.S. Pat. No. 4,199,363 and West German Patent (OLS) Nos. 2,541,274 and 2,541,230.

The color light-sensitive materials of the present invention preferably contain various antiseptics or antifungal .agents, such as phenethyl alcohol 1,2-benzisothiazolin-3-one, n-butyl p-hydroxybenzoate, phenol, 4-chloro-3,5-dimethylphenol, 2-phenoxyethanol, 2-(4-thiazolyl)benzimidazole, etc. as described in JP-A-63-257747, JP-A-62-272248, and JP-A-1-80941.

The present invention can be applied to a wide variety of color light-sensitive materials, such as color negative films for general use or for movies, color reversal films for slides or TV, color papers, color positive films, and color reversal papers.

Examples of supports which can be suitably used in the color light-sensitive materials are described, e.g., in RD, No. 17643, p. 28, ibid, No. 18716, pp. 647 (right column) to 648 (left column), and ibid, No. 307105, p. 879.

In the color light-sensitive materials of the present invention, the hydrophilic colloidal layers on the side having emulsion layers preferably have a total film thickness of not more than 28 μm, more preferably not more than 23 μm, particularly preferably not more than 18 μm, most preferably not more than 16 μm, and a rate of swelling $T_{\frac{1}{2}}$ of not more than 30 seconds, more preferably not more than 20 seconds. The terminology "total film thickness" as used herein means the film thickness as measured after conditioning at 25° C. and a relative humidity of 55% for 2 days. The terminology "rate of swelling $T_{\frac{1}{2}}$" means the time required for a color light-sensitive material to be swollen to $\frac{1}{2}$ the saturated swollen thickness, the saturated swollen thickness being defined as 90% of the maximum swollen thickness which is reached when the color light-sensitive material is swollen with a color developing solution at 30° C. for 3 minutes and 15 seconds. The rate of swelling can be determined by methods known in the art using, for example, a swellometer of the type described in A. Green et al., Photographic Science and Engineering, Vol. 19, No. 2, pp. 124–129.

The rate of swelling $T_{\frac{1}{2}}$ can be controlled by adding a proper amount of a hardening agent for a gelatin binder or by varying aging conditions after coating.

Further, the light-sensitive material preferably has a degree of swelling of from 150 to 400%. The terminology "degree of swelling" as used herein means the value obtained from the maximum swollen film thickness as defined above according the formula (maximum swollen film thickness—film thickness)/film thickness.

The light-sensitive material of the present invention preferably has at least one hydrophilic colloidal layer called a backing layer having a total dry thickness of from 2 to 20 μm on the side opposite to the emulsion layer side. The backing layers preferably contain the above-described additives, e.g., light absorbents, filter dyes, ultraviolet absorbents, antistatic agents, hardening agents, binders, plasticizers, lubricants, coating aids, and surface active agents. The backing layers preferably have a degree of swelling of from 150 to 500%.

The above-described color photographic materials can be development processed according to usual methods as described in RD, No. 17643, pp. 28–29, ibid, No. 18716, p. 615, left to right columns, and ibid, No. 307105, pp. 880–881.

A color developing solution which can be used for development processing is preferably an alkaline aqueous solution containing an aromatic primary amine color developing agent. Useful color developing agents include aminophenol compounds and preferably p-phenylenediamine compounds. Typical examples of p-phenylenediamine compounds are 3-methyl-4-amino-N,N-diethylaniline, 3-methyl-4-amino-N-ethyl-N-β-hydroxyethylaniline, 3-methyl-4-amino-N-ethyl-N-β-methanesulfonamidoethylaniline, 3-methyl-4-amino-N-ethyl-N-β-methoxyethylaniline, and salts thereof (e.g., sulfates, hydrochlorides, and p-toluenesulfonates), with 3-methyl-4-amino-N-ethyl-N-β-hydroxyethylaniline sulfate being particularly preferred. These developing agents may be used either individually or in combination of two or more thereof, according to the purpose.

The color developing solution usually contains pH buffering agents (e.g., carbonates, borates or phosphates of alkali metals) and development inhibitors or antifoggants (e.g., chlorides, bromides, iodides, benzimidazoles, benzothiazoles, and mercapto compounds). If desired, the color developing solution further contains various preservatives, such as hydroxylamine, diethylhydroxylamine, sulfites, hydrazines (e.g., N,N-biscarboxymethylhydrazine), phenyl semicarbazides, triethanolamine, and catecholsulfonic acids; organic solvents, (e.g., ethylene glycol and diethylene glycol); development accelerators (e.g., benzyl alcohol, polyethylene glycol, quaternary ammonium salts, and amines); dye-forming couplers; competing couplers; auxiliary developing agents (e.g., 1-phenyl-3-pyrazolidone); viscosity-imparting agents; and various chelating agents, such as aminopolycarboxylic acids, aminopolyphosphonic acids, alkylphosphonic acids, and phosphonocarboxylic acids (e.g., ethylenediaminetetraacetic acid, nitrilotriacetic acid, ethylenetriaminepentaacetic acid, cyclohexanediaminetetraacetic acid, hydroxyethyliminodiacetic acid, 1-hydroxyethylidene-1,1-diphosphonic acid, nitrilo-N,N,N-trimethylenephosphonic acid, ethylenediamine-N,N,N,N-tetramethylenephosphonic acid, ethylenediamine-di-o-hydroxyphenylacetic acid, and salts thereof).

For reversal processing, color development is generally preceded by black-and-white (hereinafter abbreviated as B/W) development. A B/W developing solution to be used for B/W development contains one or more of known B/W developing agents, such as dihydroxybenzenes (e.g., hydroquinone), 3-pyrazolidones (e.g., 1-phenyl-3-pyrazolidone), and aminophenols (e.g., N-methyl-p-aminophenol).

The color or B/W developing solution generally has a pH between 9 and 12. The rate of replenishment for these developing solutions, though varying depending on the kind of color photographic material to be processed, is usually not more than 3 l per $m^2$ of a light-sensitive material. The rate of replenishment can be reduced to 500 ml/$m^2$ or less by reducing the bromide ion concentration in the replenisher. When processing is carried out at a reduced rate of replenishment, it is desirable to prevent evaporation and aerial oxidation of the processing solution by minimizing the contact area of the processing solution with air.

The contact area between a photographic processing solution and air can be expressed in terms of an opening ratio calculated by dividing the contact area ($cm^2$) of the processing solution with air by a volume ($cm^3$) of the processing solution. The opening ratio as defined above is preferably not more than 0.1, and more preferably between 0.001 and 0.05.

The opening ratio of the processing tank can be so adjusted by, for example, putting a barrier, such as a floating cover, on the liquid surface, using a movable cover as described in JP-A-1-82033, or utilizing slit development processing as described in JP-A-63-216050.

Reduction of the opening ratio is preferably applied not only to color development and B/W development but also to all the subsequent steps, such as the bleach, blix, fixing, washing, and stabilization steps.

Reduction of the replenishment rate may also be achieved by using a means for suppressing the accumulation of bromide ions in the developing solution.

The processing time with the color developing solution can be from 2 to 5 minutes. The processing time may be shortened by conducting development processing at an elevated temperature and an increased pH in an increased concentration of the color developing agent.

The photographic emulsion layers after color development are usually subjected to bleach. Bleach and fixing may be carried out either simultaneously (blix) or separately. For rapid processing, bleach may be followed by blix. Further, the mode of desilvering can be selected according to the end use. For example, blix may be effected using two tanks connected, or fixing may be followed by blix, or blix may be followed by bleach.

Bleaching agents to be used include compounds of polyvalent metals (e.g., iron (III)), peracids, quinones, and nitroso compounds. Typical bleaching agents include organic complex salts of iron (III), such as complex salts with aminopolycarboxylic acids (e.g., ethylenediaminetetraacetic acid, diethylenetriaminepentaacetic acid, cyclohexanediaminetetraacetic acid, methyliminodiacetic acid, 1,3-diaminopropanoltetraacetic acid, glycol ether diaminetetraacetic acid), citric acid, tartaric acid, or malic acid. Aminopolycarboxylic acid iron (III) complexes (e.g., (ethylenediaminetetraacetato)iron (III) salts and (1,3-diaminopropanetetraacetato)iron (III) salts) are preferred as bleaching agents from the standpoint of rapid processing and prevention of environmental pollution. Aminopolycarboxylic acid iron (III) complex salts are particularly useful either in a bleaching bath or in a blix monobath. A bleaching bath or blix bath containing these aminopolycarboxylic acid iron (III) complex salts usually has a pH between 4.0 and 8.0. A lower pH can also be employed for rapid processing.

If desired, a fixing bath, a blix bath, or a prebath thereof may contain known bleaching accelerators. Useful bleaching accelerators include compounds having a mercapto group or a disulfide group as described in U.S. Pat. No. 3,893,858, German Patents 1,290,812 and 2,059,988, JP-A-53-32736, JP-A-53-57831, JP-A-53-37418, JP-A-53-72623, JP-A-53-95630, JP-A-53-95631, JP-A-53-104232, JP-A-53-124424, JP-A-53-141623, JP-A-53-28426, and RD, No. 17129 (Jul., 1978); thiazolidine derivatives as described in JP-A-50-140129; thiourea derivatives as described in JP-B-45-8506, JP-A-52-20832, JP-A-53-32735, and U.S. Pat. No. 3,706,561; iodides as described in West German Patent 1,127,715 and JP-A58-16235; polyoxyethylene compounds as described in German Patents 966,410 and 2,748,430; polyamine compounds as described in JP-B-45-8836; compounds as described in JP-A-49-40943, JP-A-49-59644, JP-A-53-94927, JP-A-54-35727, JP-A-55-26506, and JP-A-58-163940; and bromide ions. Among these bleaching accelerators, compounds having a mercapto group or a disulfide group are preferred because of their high accelerating effect. The compounds disclosed in U.S. Pat. No. 3,893,858, West German Patent 1,290,812, and JP-A-53-95630 are particularly preferred. In addition, the compounds disclosed in U.S. Pat. No. 4,552,834 are also preferred. These bleaching accelerators may be incorporated into a light-sensitive material. The bleaching accelerators are particularly effective for blix of color light-sensitive materials used in camera.

For the purpose of preventing bleach stain, the bleaching or blix bath preferably contains organic acids. Particularly preferred organic acids used to achieve this effect are those having an acid dissociation constant (pKa) of from 2 to 5 (e.g., acetic acid, propionic acid, and hydroxyacetic acid).

Fixing agents which can be used in a fixing or blix bath include thiosulfates, thiocyanates, thioether compounds, thioureas, and a large quantity of an iodide, with thiosulfates being commonly employed. In particular, ammonium thiosulfate is highly useful. The combined use of a thiosulfate and a thiocyanate, a thioether compound, a thiourea, etc., is also preferred. Preservatives for the fixing or blix bath preferably include sulfites, bisulfites, carbonyl-bisulfite adducts, and sulfinic acid compounds described in EP 294769A.

The fixing or blix bath preferably contains various aminopolycarboxylic acids or organophosphonic acids for stabilization.

Further, the fixing or blix bath preferably contains 0.1 to 10 mol/l of compounds having a pKa of from 6.0 to 9.0 for pH adjustment, preferably imidazoles (e.g., imidazole, 1-methylimidazole, 1-ethylimidazole, and 2-methylimidazole).

The total desilvering time is preferably as short as possible, as long as insufficient desilvering does not result. A preferred desilvering time is from 1 to 3 minutes, more preferably from 1 to 2 minutes. The desilvering temperature is from 25° to 50° C., preferably from 35° to 45° C. In the preferred temperature range, the rate of desilvering is improved, and stain formation after processing is effectively prevented.

It is desirable that desilvering should be performed while reinforcing stirring as much as possible. Methods or means for achieving reinforced stirring include a method in which a jet stream of a processing solution is made to strike against the surface of the emulsion layer as described in JP-A-62-183460; a method of using a rotating means to enhance stirring effects as described in JP-A-62-183461; a method in which a light-sensitive material is moved with its emulsion surface being in contact with a wire blade placed in a processing solution to create turbulence; and a method of increasing the total flow of a circulating processing solution. These stirring means are effective in any of a bleaching bath, a blix bath and a fixing bath. Reinforced stirring appears to accelerate supply of the bleaching agent or the fixing agent to emulsion layers and, as a result, to increase the rate of desilvering.

The above-described means for reinforced stirring is more effective in the case where a bleaching accelerator is used, markedly enhancing acceleration effects and eliminating the fixing inhibitory effect of the bleaching accelerator.

An automatic developing machine which can be used for processing the light-sensitive material preferably has a means for carrying a light-sensitive material as described in JP-A-60-191257, JP-A-60-191258, and JP-A-60-191259. As mentioned in JP-A-60-191257, supra, such a carrying means is highly effective to considerably reduce carry-over of the processing solution from a prebath into a succeeding bath, thereby preventing reduction of processing capacity. This means is particularly effective for reduction of the processing time or replenishment rate in each processing step.

The silver halide color light-sensitive material after desilvering is generally subjected to washing and/or stabilization.

The amount of washing water to be used in the washing step is selected from a broad range depending on characteristics of the light-sensitive material (e.g., the kind of components in the photographic materials, such as couplers), the end use of the light-sensitive material, the temperature of the washing water, the number of washing tanks (the number of stages), the replenishing system (e.g., counter-flow system or direct-flow system), and other various conditions. For example, a relation between the number of washing tanks and the quantity of water in a multi-stage counter-flow system can be obtained by the method described in *Journal of the Society of Motion Picture and Television Engineers*, Vol. 64, pp. 248-253 (May, 1955).

According to the disclosed multi-stage counter-flow system, the required amount of water can be greatly reduced. However, bacteria tend to grow in the tank with an increase in water retention time, and suspended bacterial cells adhere to light-sensitive materials. Such a problem can be effectively addressed by adopting a method of reducing the amount calcium and magnesium ions in the washing water as described in JP-A-62-288838. It is also effective to use bactericides, such as isothiazolone compounds or thiabendazole compounds as described in JP-A-57-8542; chlorine-type bactericides (e.g., chlorinated sodium isocyanurate); and bactericides described in Horiguchi Hiroshi, *Bokin Bobaizai no Kagaku*, (Sankyo Shuppan, 1986), Eisei Gijutsukai (ed.), *Biseibutsu no Mekkin, Sakkin, Bobai Gijutsu*, (Kogyo Gijutsukai, 1982), and Nippon Bokin Bobai Gakkai (ed.), *Bokin Bobaizai Jiten* (1986) (e.g., benzotriazole).

Washing water usually has a pH between 4 and 9, preferably between 5 and 8. Washing conditions, though varying depending on the characteristics or the end use of the light-sensitive material and the like, are usually from 15° to 45° C. in temperature and from 20 seconds to 10 minutes in time, preferably from 25 to 40° C. in temperature and from 30 seconds to 5 minutes in time.

The washing step may be replaced with stabilization processing step. Where stabilization is conducted in place of washing, any of known stabilizing techniques described (e.g., in JP-A-57-8543, JP-A-58-14834, and JP-A-60-220345) can be utilized. Where washing is followed by stabilization, the stabilizing bath to be used includes a solution containing a dye stabilizer and a surface active agent, which is used as a final bath for color light-sensitive materials used in camera. Suitable dye stabilizers include aldehydes (e.g., formalin and glutaraldehyde), N-methylol compounds, hexamethylenetetramine, and an aldehyde-sulfite adduct. If desired, the stabilizing bath may also contain various chelating agents and antifungal agents.

The overflow accompanying replenishment for washing and/or stabilization may be reused in other processing steps, such as a desilvering step.

In cases where each processing solution is concentrated by vaporization during processing with an automatic developing machine, water is preferably supplied to the processing solution for correction of the concentration.

For the purpose of simplifying the processing and enhancing the processing speed, the silver halide color light-sensitive material may contain therein a color developing agent, preferably in the form of a precursor thereof. Examples of color developing agent precursors include. indoaniline compounds described in U.S. Pat. No. 3,342,597, Schiff base compounds described in U.S. Pat. No. 3,342,599 and RD, Nos. 14850 and 15159, aldol compounds described in RD, No. 13924, metal complex salts described in U.S. Pat. No. 3,719,492, and urethane compounds described in JP-A-53-135628.

If desired, the silver halide color light-sensitive material may further contain therein various -phenyl-3-pyrazolidone compounds for the purpose of accelerating color development. Typical examples of these accelerators are described in JP-A-56-64339, JP-A-57-144547, and JP-A-58-115438.

Each of the above-described processing solutions is used at a temperature of from 10° to 50° C. and, in a standard manner, from 33° C. to 38° C. Higher processing temperatures may be employed for reducing processing time, or lower temperatures may be employed for improving image quality or stability of the processing solution.

The prevent invention is also applicable to heat-developable light-sensitive materials described in U.S. Pat. No. 4,500,626, JP-A-60-133449, JP-A-59-218443, JP-A-61-238056, and EP 210,660A2.

The present invention is now illustrated in greater detail by way of the following examples, but it should be understood that the present invention is not deemed to be limited thereto. All parts, percents and ratios are by weight unless otherwise indicated.

EXAMPLE 1

The following layers were coated on a cellulose triacetate film support having a subbing layer to prepare a multi-layer color light-sensitive material. The resulting material was designated Sample 101. Abbreviations of additives used herein were taken from the activity or typical activity thereof as follows.

UV ... Ultraviolet absorbent
Solv ... High-boiling organic solvent
ExF ... Dye
ExS ... Sensitizing dye
ExC ... Cyan coupler
ExM ... Magenta coupler
ExY ... Yellow coupler
Cpd, F, B ... Additive compound
H ... Hardening agent
W ... Surface active agent

| 1st Layer (Antihalation Layer): | |
|---|---|
| Black colloidal silver | 0.15 g-Ag/m$^2$ |
| Gelatin | 2.33 g/m$^2$ |
| ExM-6 | 0.11 g/m$^2$ |
| UV-1 | $3.0 \times 10^{-2}$ g/m$^2$ |
| UV-2 | $6.0 \times 10^{-2}$ g/m$^2$ |
| UV-3 | $7.0 \times 10^{-2}$ g/m$^2$ |
| Solv-1 | 0.16 g/m$^2$ |
| Solv-2 | 0.10 g/m$^2$ |
| ExF-1 | $1.0 \times 10^{-2}$ g/m$^2$ |
| ExF-2 | $4.0 \times 10^{-2}$ g/m$^2$ |
| ExF-3 | $5.0 \times 10^{-3}$ g/m$^2$ |

-continued

| | |
|---|---|
| Cpd-6 | $1.0 \times 10^{-3}$ g/m$^2$ |
| 2nd Layer (Low Sensitive Red-Sensitive Emulsion Layer): | |
| Silver iodobromide emulsion (AgI content: 4.0 mol %; uniform AgI type; sphere-equivalent diameter: 0.35 μm; coefficient of variation of sphere-equivalent diameter: 18%; tabular grains; aspect ratio: 3.0) | 0.35 g-Ag/m$^2$ |
| Silver iodobromide emulsion (AgI content: 6.0 mol %; high AgI inside type; core/shell Ag ratio of 1:2; sphere-equivalent diameter: 0.40 μm; coefficient of variation of sphere-equivalent diameter: 18%; tabular grains; aspect ratio: 2.0) | 0.18 g-Ag/m$^2$ |
| Gelatin | 0.77 g/m$^2$ |
| ExS-1 | $2.4 \times 10^{-4}$ mol/mol-AgX (X: halogen) |
| ExS-2 | $1.4 \times 10^{-4}$ mol/mol-AgX |
| ExS-5 | $2.3 \times 10^{-4}$ mol/mol-AgX |
| ExS-7 | $4.1 \times 10^{-6}$ mol/mol-AgX |
| ExC-1 | 0.17 g/m$^2$ |
| ExC-2 | $4.0 \times 10^{-2}$ g/m$^2$ |
| ExC-3 | $8.0 \times 10^{-2}$ g/m$^2$ |
| 3rd Layer (Middle Sensitive Red-Sensitive Emulsion Layer): | |
| Silver iodobromide emulsion (AgI content: 6.0 mol %; high AgI inside type; core/shell Ag ratio of 1:2; sphere-equivalent diameter: 0.50 μm; coefficient of variation of sphere-equivalent diameter: 19%; tabular grains; aspect ratio: 5.5) | 0.80 g-Ag/m$^2$ |
| Gelatin | 1.46 g/m$^2$ |
| ExS-1 | $2.4 \times 10^{-4}$ mol/mol-AgX |
| ExS-2 | $1.4 \times 10^{-4}$ mol/mol-AgX |
| ExS-5 | $2.4 \times 10^{-4}$ mol/mol-AgX |
| ExS-7 | $4.3 \times 10^{-6}$ mol/mol-AgX |
| ExC-1 | 0.38 g/m$^2$ |
| ExC-2 | $2.0 \times 10^{-2}$ g/m$^2$ |
| ExC-3 | 0.12 g/m$^2$ |
| ExM-7 | $3.0 \times 10^{-2}$ g/m$^2$ |
| UV-2 | $5.7 \times 10^{-2}$ g/m$^2$ |
| UV-3 | $5.7 \times 10^{-2}$ g/m$^2$ |
| 4th Layer (High Sensitive Red-Sensitive Emulsion Layer): | |
| Silver iodobromide emulsion (AgI content: 9.3 mol %; multiple structure grains; core/shell Ag ratio: 3:4:2; core/middle/shell AgI content: 24/0/6 mol %; sphere-equivalent diameter: 0.70 μm; coefficient of variation of sphere-equivalent diameter: 20%; tabular grains; aspect ratio: 6.5) | 1.49 g-Ag/m$^2$ |
| Gelatin | 1.38 g/m$^2$ |
| ExS-1 | $2.0 \times 10^{-4}$ mol/mol-AgX |
| ExS-2 | $1.1 \times 10^{-4}$ mol/mol-AgX |
| ExS-5 | $1.9 \times 10^{-4}$ mol/mol-AgX |
| ExS-7 | $1.4 \times 10^{-5}$ mol/mol-AgX |
| ExC-1 | $8.0 \times 10^{-2}$ g/m$^2$ |
| ExC-4 | $9.0 \times 10^{-2}$ g/m$^2$ |
| Solv-1 | 0.20 g/m$^2$ |
| Solv-2 | 0.53 g/m$^2$ |
| 5th Layer (Intermediate Layer): | |
| Gelatin | 0.62 g/m$^2$ |
| Cpd-1 | 0.13 g/m$^2$ |
| Polyethyl acrylate latex | $8.0 \times 10^{-2}$ g/m$^2$ |
| Solv-1 | $8.0 \times 10^{-2}$ g/m$^2$ |
| 6th Layer (Low Sensitive Green-Sensitive Emulsion Layer): | |
| Silver iodobromide emulsion (AgI content: 4.0 mol %; uniform AgI type; sphere-equivalent diameter: 0.33 μm; coefficient of variation of sphere-equivalent diameter: 37%; tabular grains; aspect ratio: 2.0) | 0.19 g-Ag/m$^2$ |
| Gelatin | 0.44 g/m$^2$ |
| ExS-3 | $1.5 \times 10^{-4}$ mol/mol-AgX |
| ExS-4 | $4.4 \times 10^{-4}$ mol/mol-AgX |
| ExS-5 | $9.2 \times 10^{-5}$ mol/mol-AgX |
| ExM-5 | 0.17 g/m$^2$ |
| ExM-7 | $3.0 \times 10^{-2}$ g/m$^2$ |
| Solv-1 | 0.13 g/m$^2$ |
| Solv-2 | $1.0 \times 10^{-2}$ g/m$^2$ |
| 7th Layer (Middle Sensitive Green-Sensitive Emulsion Layer): | |
| Silver iodobromide emulsion (AgI content: 4.0 mol %; uniform AgI type; sphere-equivalent diameter: 0.55 μm; coefficient of variation of sphere-equivalent diameter: 15%; tabular grains; aspect ratio: 4.0) | 0.24 g-Ag/m$^2$ |
| Gelatin | 0.54 g/m$^2$ |
| ExS-3 | $2.1 \times 10^{-4}$ mol/mol-AgX |
| ExS-4 | $6.3 \times 10^{-4}$ mol/mol-AgX |
| ExS-5 | $1.3 \times 10^{-4}$ mol/mol-AgX |
| ExM-5 | 0.15 g/m$^2$ |
| ExM-7 | $4.0 \times 10^{-2}$ g/m$^2$ |
| ExY-8 | $3.0 \times 10^{-2}$ g/m$^2$ |
| Solv-1 | 0.13 g/m$^2$ |
| Solv-2 | $1.0 \times 10^{-2}$ g/m$^2$ |
| 8th Layer (High Sensitive Green-Sensitive Emulsion Layer): | |
| Silver iodobromide emulsion (AgI content: 8.8 mol %; multiple structure of core/middle/shell Ag ratio: 3:4:2; core/middle/shell AgI content: 24/0/3 mol %; sphere-equivalent diameter: 0.75 μm; coefficient of variation of sphere-equivalent diameter: 23%; tabular grains; aspect ratio: 1.6) | 0.49 g-Ag/m$^2$ |
| Gelatin | 0.61 g/m$^2$ |
| ExS-4 | $4.3 \times 10^{-4}$ mol/mol-AgX |
| ExS-5 | $8.6 \times 10^{-5}$ mol/mol-AgX |
| ExS-8 | $2.8 \times 10^{-5}$ mol/mol-AgX |
| ExM-5 | $8.0 \times 10^{-2}$ g/m$^2$ |
| ExM-6 | $3.0 \times 10^{-2}$ g/m$^2$ |
| ExY-8 | $3.0 \times 10^{-2}$ g/m$^2$ |
| ExC-1 | $1.0 \times 10^{-2}$ g/m$^2$ |
| ExC-4 | $1.0 \times 10^{-2}$ g/m$^2$ |
| Solv-1 | 0.23 g/m$^2$ |
| Solv-2 | $5.0 \times 10^{-2}$ g/m$^2$ |
| Solv-4 | $1.0 \times 10^{-2}$ g/m$^2$ |
| Cpd-8 | $1.0 \times 10^{-2}$ g/m$^2$ |
| 9th Layer (Intermediate Layer): | |
| Gelatin | 0.56 g/m$^2$ |
| Cpd-1 | $4.0 \times 10^{-2}$ g/m$^2$ |
| Polyethyl acrylate latex | $5.0 \times 10^{-2}$ g/m$^2$ |
| Solv-1 | $3.0 \times 10^{-2}$ g/m$^2$ |
| UV-4 | $3.0 \times 10^{-2}$ g/m$^2$ |
| UV-5 | $4.0 \times 10^{-2}$ g/m$^2$ |
| 10th Layer (Layer Donating Interlayer Effect to Red-Sensitive Layer): | |
| Silver iodobromide emulsion (AgI content: 8.0 mol %; high AgI inside type; core/shell Ag ratio: 1:2; sphere-equivalent diameter: 0.65 μm; coefficient of variation of sphere-equivalent diameter: 25%; tabular grains; aspect ratio: 2.0) | 0.67 g-Ag/m$^2$ |
| Silver iodobromide emulsion (AgI | 0.20 g-Ag/m$^2$ |

-continued

| | |
|---|---|
| content: 4.0 mol %; uniform AgI type; sphere-equivalent diameter: 0.4 μm; coefficient of variation of sphere-equivalent diameter: 30%; tabular grains; aspect ratio: 3.0) | |
| Gelatin | 0.87 g/m² |
| ExS-3 | 6.7 × 10⁻⁴ mol/mol-AgX |
| ExM-10 | 0.16 g/m² |
| Solv-1 | 0.30 g/m² |
| Solv-6 | 3.0 × 10⁻² g/m² |
| 11th Layer (Yellow Filter Layer): | |
| Yellow colloidal silver | 9.0 × 10⁻² g/m² |
| Gelatin | 0.84 g/m² |
| Cpd-2 | 0.13 g/m² |
| Solv-1 | 0.13 g/m² |
| Cpd-1 | 8.0 × 10⁻² g/m² |
| Cpd-6 | 2.0 × 10⁻³ g/m² |
| H-1 | 0.25 g/m² |
| 12th Layer (Low Sensitive Blue-Sensitive Emulsion Layer): | |
| Silver iodobromide emulsion (AgI content: 6.5 mol %; uniform AgI type; sphere-equivalent diameter: 0.50 μm; coefficient of variation of sphere-equivalent diameter: 15%; tabular grains; aspect ratio: 7.0) | 0.50 g-Ag/m² |
| Silver iodobromide emulsion (AgI content: 3.0 mol %; uniform AgI type; sphere-equivalent diameter: 0.3 μm; coefficient of variation of sphere-equivalent diameter: 30%; tabular grains; aspect ratio: 7.0) | 0.30 g-Ag/m² |
| Gelatin | 2.18 g/m² |
| ExS-6 | 9.0 × 10⁻⁴ mol/mol-AgX |
| ExC-1 | 0.14 g/m² |
| ExY-9 | 0.17 g/m² |
| ExY-11 | 1.09 g/m² |
| Solv-1 | 0.54 g/m² |
| 13th Layer (Intermediate Layer): | |
| Gelatin | 0.40 g/m² |
| ExY-12 | 0.19 g/m² |
| Solv-1 | 0.19 g/m² |
| 14th Layer (High Sensitive Blue-Sensitive Emulsion Layer): | |
| Silver iodobromide emulsion (AgI content: 10.0 mol %; high AgI inside type; core/shell Ag ratio: 2:1; sphere equivalent diameter: | 0.40 g-Ag/m² |

-continued

| | |
|---|---|
| 1.0 μm; cofficient of variation of sphere-equivalent diameter: 25%; multiple twinned tabular grains; aspect ratio: 2.0) | |
| Gelatin | 0.49 g/m² |
| ExS-6 | 2.6 × 10⁻⁴ mol/mol-AgX |
| ExY-9 | 1.0 × 10⁻² g/m² |
| ExY-11 | 0.20 g/m² |
| ExC-1 | 1.0 × 10⁻² g/m² |
| Solv-1 | 9.0 × 10⁻² g/m² |
| 15th Layer (1st Protective Layer): | |
| Silver iodobromide fine grain emulsion (AgI content: 2.0 mol %; uniform AgI type; sphere-equivalent diameter: 0.07 μm) | 0.12 g-Ag/m² |
| Gelatin | 0.63 g/m² |
| UV-4 | 0.11 g/m² |
| UV-5 | 0.18 g/m² |
| Solv-5 | 2.0 × 10⁻² g/m² |
| Cpd-5 | 0.10 g/m² |
| Polyethyl acrylate latex | 9.0 × 10⁻² g/m² |
| 16th Layer (2nd Protective Layer): | |
| Silver iodobromide fine grain emulsion (AgI content: 2.0 mol %; uniform AgI type; sphere-equivalent diameter: 0.07 μm) | 0.36 g-Ag/m² |
| Gelatin | 0.85 g/m² |
| B-1 (diameter: 1.5 μm) | 8.0 × 10⁻² g/m² |
| B-2 (diameter: 1.5 μm) | 8.0 × 10⁻² g/m² |
| B-3 | 2.0 × 10⁻² g/m² |
| W-4 | 2.0 × 10⁻² g/m² |
| H-1 | 0.18 g/m² |

In addition to the above-described additives, 1,2-benzisothiazolin-3-one, n-butyl p-hydroxybenzoate, and 2-phenoxyethanol were added to the sample in amounts of about 200 ppm, about 1,000 ppm, and about 10,000 ppm, respectively, based on the total amount of gelatin in the sample. The sample further contained B-4, B-5, F-1, F-2, F-3, F-4, F-5, F-6, F-7, F-8, F-9, F-10, F-11, F-12, F-13, and an iron, lead, gold, platinum, iridium or rhodium salt.

Each layer further contained surface active agents W-1, W-2 and W-3 as coating aids or emulsifying and dispersing agents.

Additives used in the sample preparation are shown below.

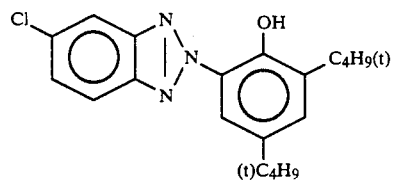

UV-1

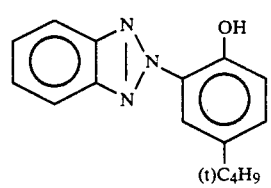

UV-2

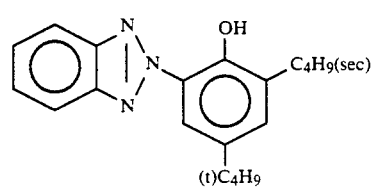

UV-3

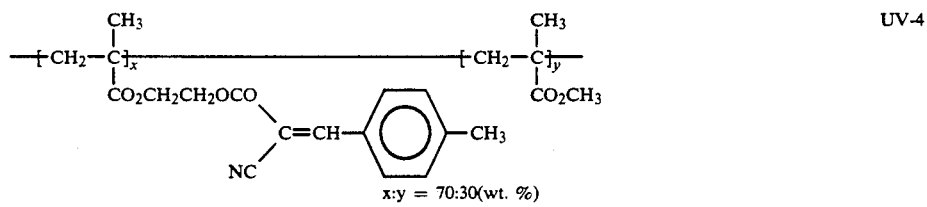 UV-4
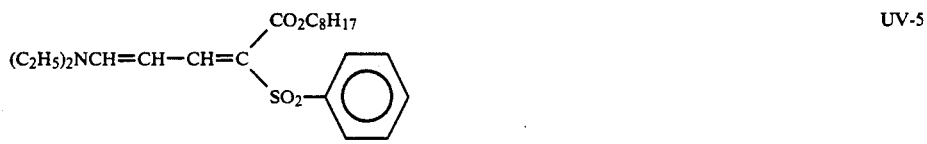 UV-5
Tricresyl phosphate — Solv-1
Dibutyl phthalate — Solv-2
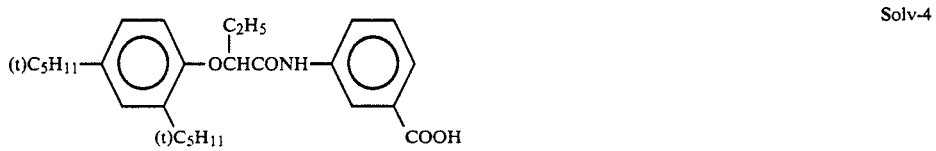 Solv-4
Trihexyl phosphate — Solv-5
 Solv-6
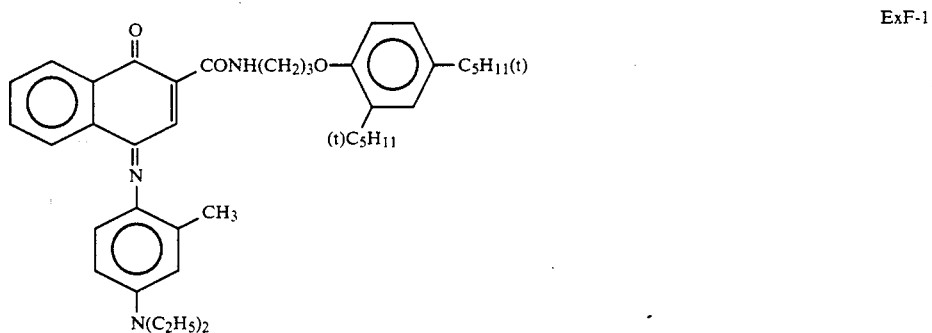 ExF-1
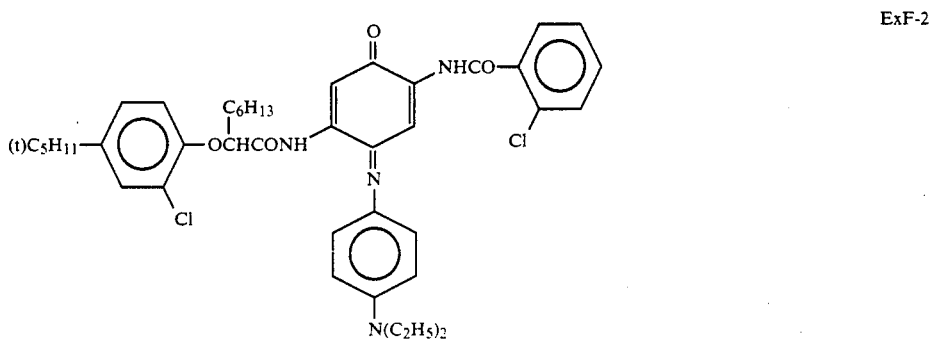 ExF-2

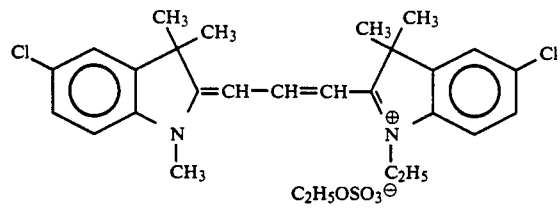
ExF-3
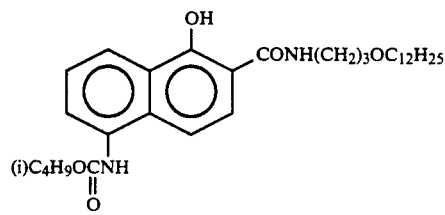
ExC-1
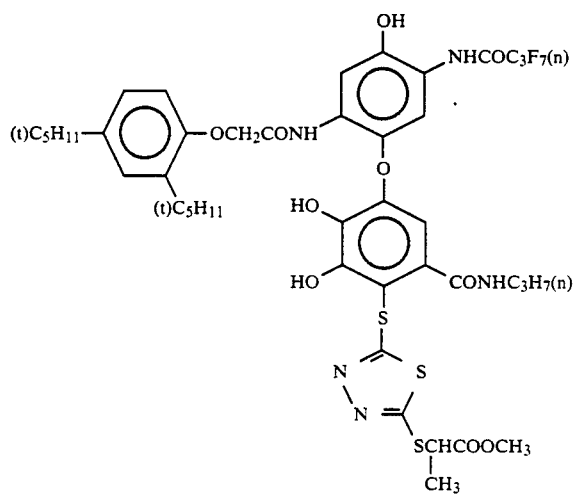
ExC-2
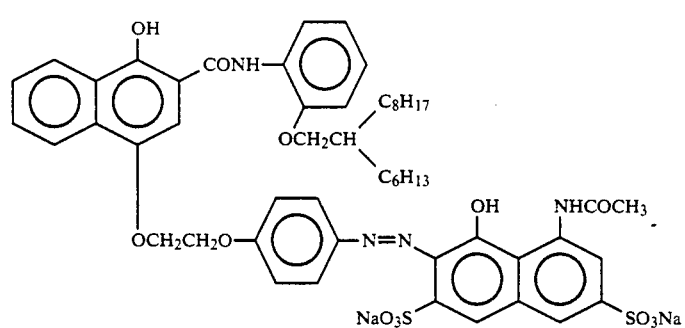
ExC-3
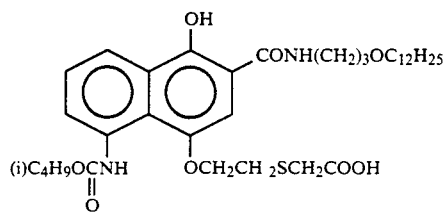
ExC-4

-continued
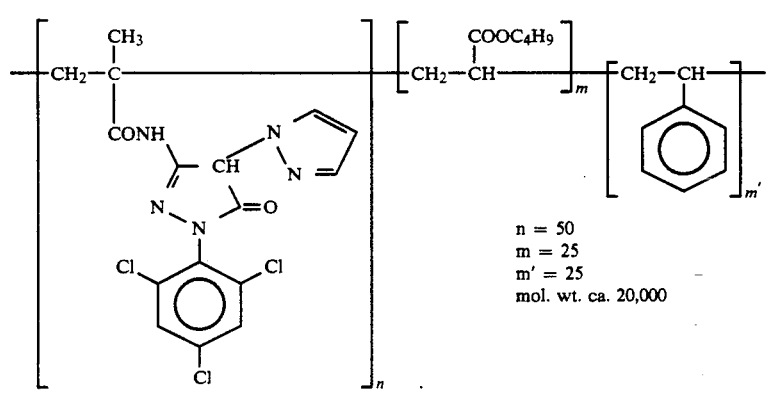 ExM-5
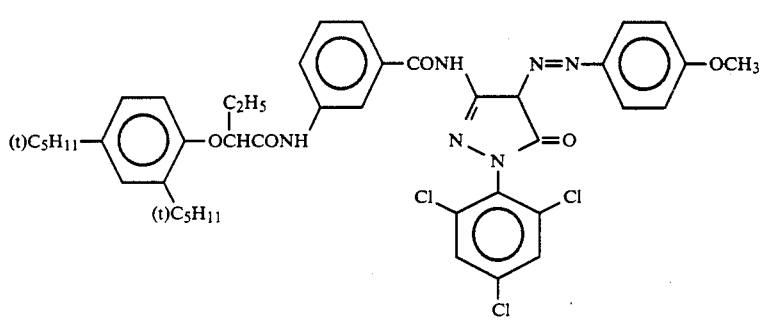 ExM-6
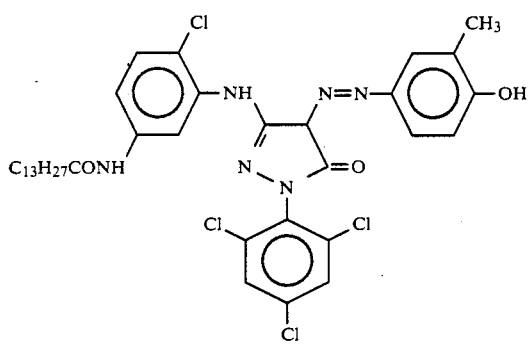 ExM-7
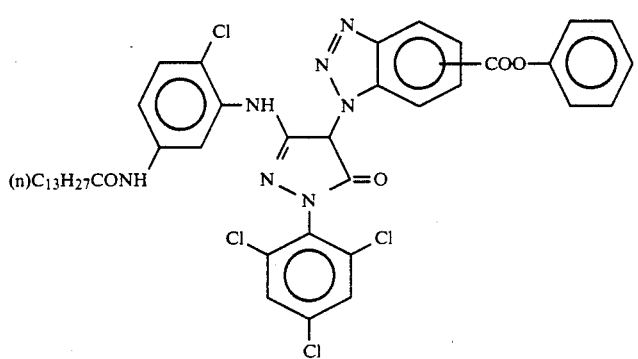 ExM-10

ExY-8
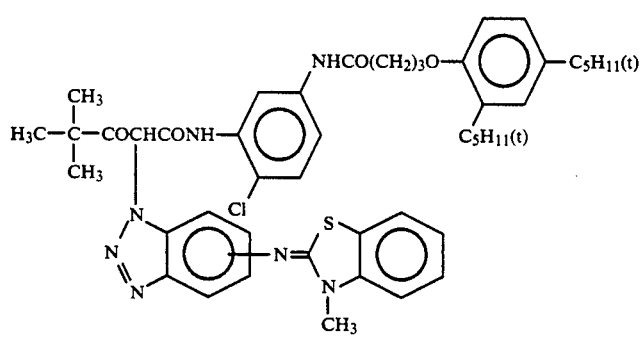
ExY-9
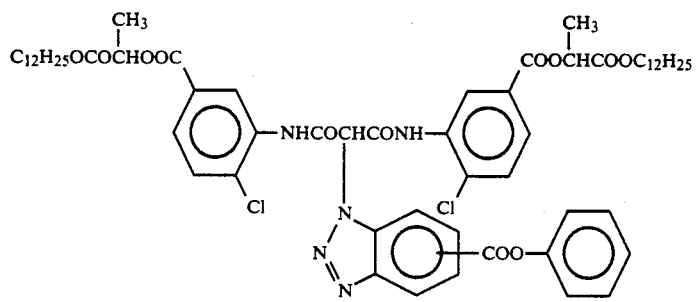
(disclosed in U.S. Patent 4,447,563, Claims)
ExY-11
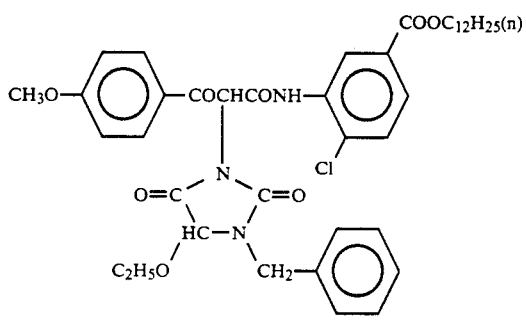
ExY-12
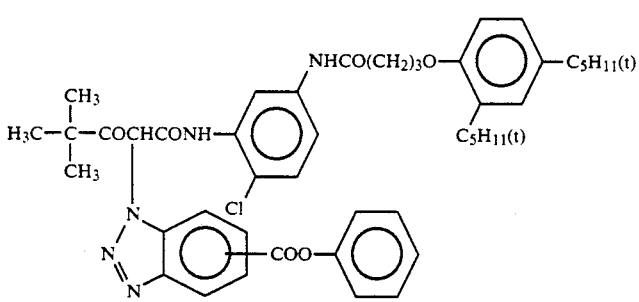
Cpd-1
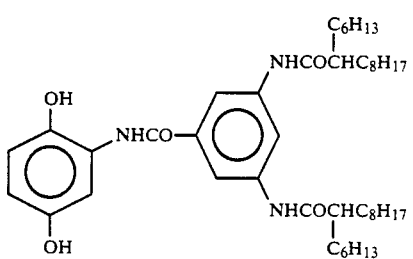
Cpd-2
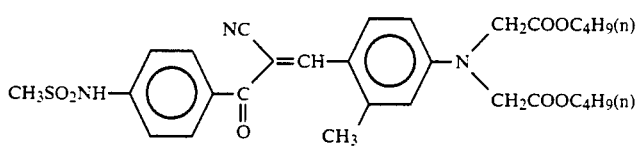

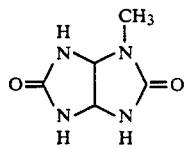
Cpd-5
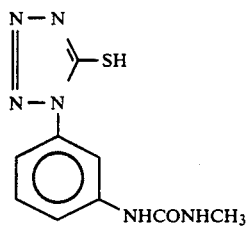
Cpd-6
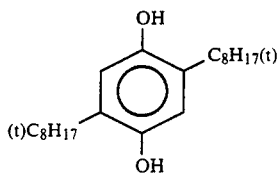
Cpd-8
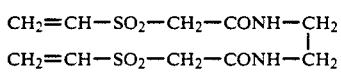
H-1
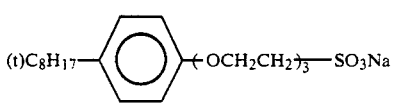
W-1
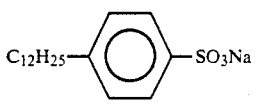
W-2
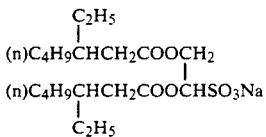
W-3
$C_8F_{17}SO_2N(C_3H_7)CH_2COOK$  W-4
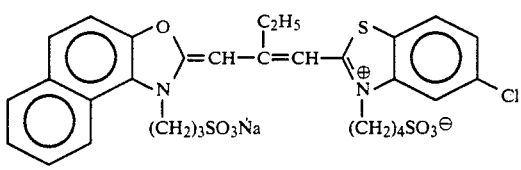
ExS-1
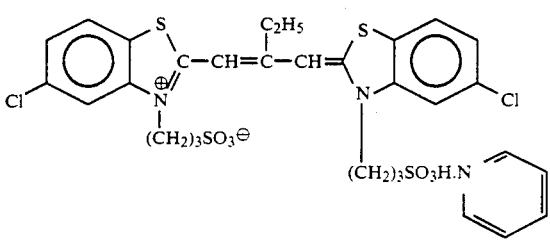
ExS-2

-continued
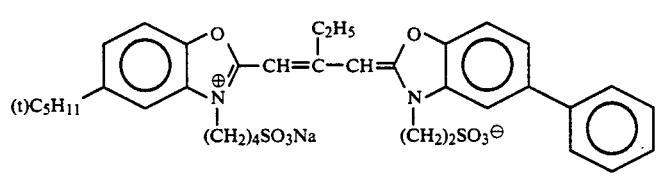 ExS-3
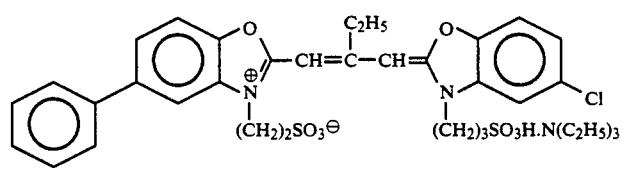 ExS-4
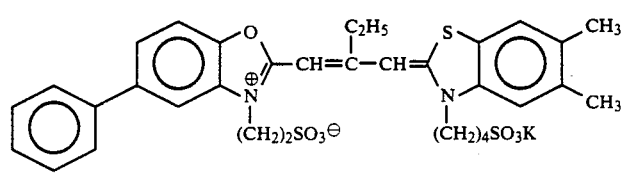 ExS-5
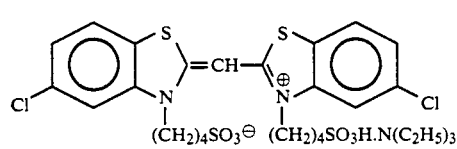 ExS-6
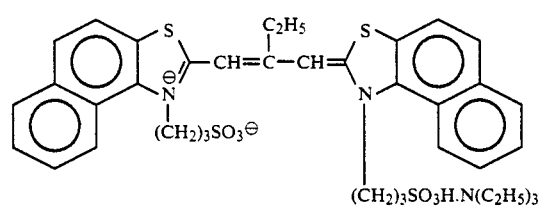 ExS-7
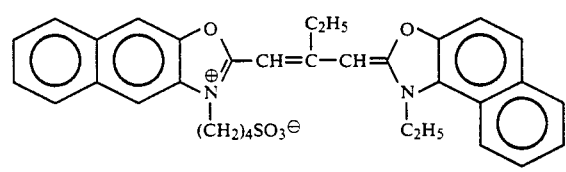 ExS-8
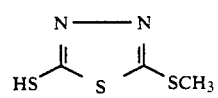 F-1
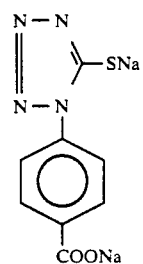 F-2

-continued
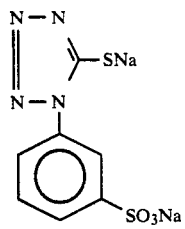
F-3
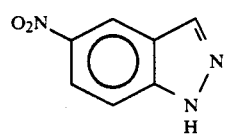
F-4
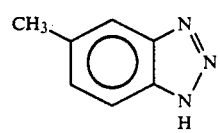
F-5
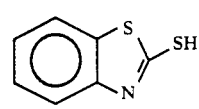
F-6
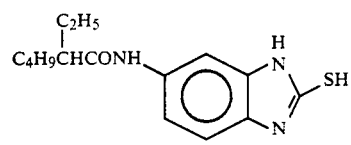
F-7
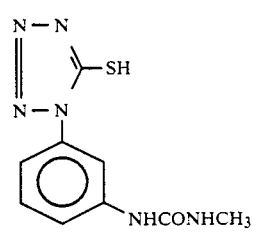
F-8
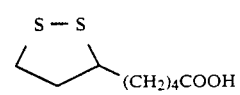
F-9
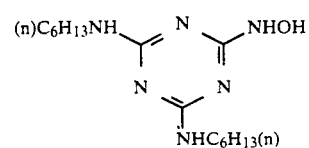
F-10
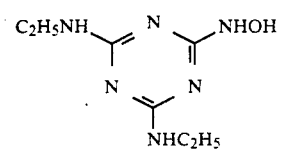
F-11
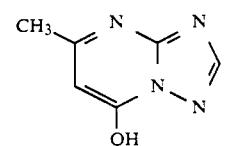
F-12

F-13
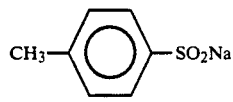

B-1
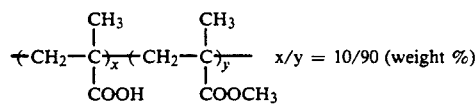  x/y = 10/90 (weight %)

B-2
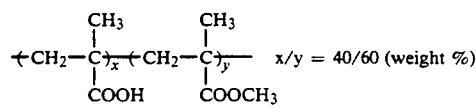  x/y = 40/60 (weight %)

B-3
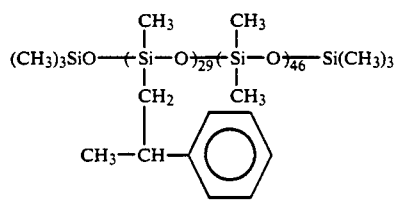

B-4
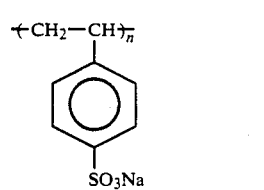

B-5
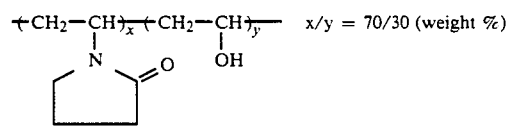  x/y = 70/30 (weight %)

Samples 102 to 111 were prepared in the same manner as Sample 101 was prepared, except for replacing ExY-9 in the 12th layer with the same weight of each of the couplers shown in Table 1 below.

Evaluations

Each sample was wedgewise exposed to white light and subjected to color development processing as described below. Thereafter, the processed sample was allowed to stand at 65° C. and 70% RH (relative humidity) for 14 days. Image stability was then evaluated by determining the decrease in yellow density at the area having a yellow density of 2.0 immediately after the processing.

Further, the processed sample was irradiated with soft X-rays through an aperture of 500 $\mu m \times 4$ cm and an aperture of 15 $\mu m \times 4$ cm, and the yellow density ratio at the center of each sample was obtained to evaluate the edge effect.

The results of these evaluations are shown in Table 1.

| Color Development Processing: | | | | |
|---|---|---|---|---|
| Step | Time | Temp. | Rate of Replenishment* | Volume of Tank |
| Color Development | 3 min 15 sec | 38° C. | 33 ml | 20 l |
| Bleach | 6 min 30 sec | 38° C. | 25 ml | 40 l |
| Washing | 2 min 10 sec | 24° C. | 1200 ml | 20 l |
| Fixing | 4 min 20 sec | 38° C. | 25 ml | 30 l |
| Washing (1) | 1 min 05 sec | 24° C. | ** | 10 l |
| Washing (2) | 1 min 00 sec | 24° C. | 1200 ml | 10 l |

| -continued | | | | |
|---|---|---|---|---|
| Color Development Processing: | | | | |
| Step | Time | Temp. | Rate of Replenishment* | Volume of Tank |
| Stabilization | 1 min 05 sec | 38° C. | 25 ml | 10 l |
| Drying | 4 min 20 sec | 55° C. | | |

Note:
*Per meter length of 35 mm wide film
**Counter-flow system from (2) to (1)

The processing solutions used had the following formulations.

| | Running Solution (g) | Replenisher (g) |
|---|---|---|
| Color Developing Solution Formulation: | | |
| Diethylenetriaminepentaacetic acid | 1.0 | 1.1 |
| 1-Hydroxyethylidene-1,1-diphosphonic acid | 3.0 | 3.2 |
| Sodium sulfite | 4.0 | 4.4 |
| Potassium carbonate | 30.0 | 37.0 |
| Potassium bromide | 1.4 | 0.7 |
| Potassium iodide | 1.5 mg | — |
| Hydroxylamine sulfate | 2.4 | 2.8 |
| 4-[N-Ethyl-N-8-hydroxyethylamino]-2-methylaniline sulfate | 4.5 | 5.5 |
| Water to make | 1.0 l | 1.0 l |
| pH | 10.05 | 10.10 |
| Bleaching Solution Formulation: | | |
| Sodium (ethylenediaminetetraacetato)iron (III) trihydrate | 100.0 | 120.0 |

|  | Running Solution (g) | Replenisher (g) |
|---|---|---|
| Disodium ethylenediaminetetraacetate | 10.0 | 10.0 |
| Ammonium bromide | 140.0 | 160.0 |
| Ammonium nitrate | 30.0 | 35.0 |
| Aqueous ammonia (27%) | 6.5 ml | 4.0 l |
| Water to make | 1.0 l | 1.0 l |
| pH | 6.0 | 5.7 |
| Fixing Solution Formulation: | | |
| Disodium ethylenediaminetetraacetate | 0.5 | 0.7 |
| Sodium sulfite | 7.0 | 8.0 |
| Sodium bisulfite | 5.0 | 5.5 |
| Aqueous ammonium thiosulfate | 170.0 ml | 200.0 ml |
| solution (70%) | | |
| Water to make | 1.0 l | 1.0 l |
| pH | 6.7 | 6.6 |
| Stabilizing Solution Formulation: | | |
| Formalin (37%) | 2.0 ml | 3.0 ml |
| Polyoxyethylene p-mononyl phenyl ether (average degree of polymerization: 10) | 0.3 | 0.45 |
| Disodium ethylenediaminetetraacetate | 0.05 | 0.08 |
| Water to make | 1.0 l | 1.0 l |
| pH | 5.0–8.0 | 5.0–8.0 |

TABLE 1

| Sample No. | Coupler in 12th Layer | Image Stability (Dmax) | Edge Effect |
|---|---|---|---|
| 101 (Comparison) | ExY-9 | 0.28 | 1.22 |
| 102 (Comparison) | RC-1 | 0.19 | 1.22 |
| 103 (Comparison) | RC-2 | 0.18 | 1.22 |
| 104 (Comparison) | RC-3 | 0.16 | 1.21 |
| 105 (Invention) | (1) | 0.04 | 1.25 |
| 106 (Invention) | (6) | 0.04 | 1.24 |
| 107 (Invention) | (9) | 0.04 | 1.25 |
| 108 (Invention) | (13) | 0.05 | 1.24 |
| 109 (Invention) | (17) | 0.05 | 1.24 |
| 110 (Invention) | (23) | 0.05 | 1.25 |
| 111 (Invention) | (25) | 0.05 | 1.24 |

RC-1: (Coupler (10) disclosed in JP-A-2-28645)

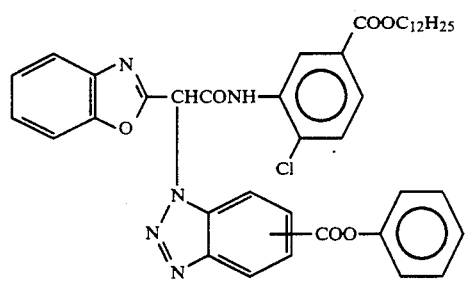

RC-2: (Coupler (2), idid.)

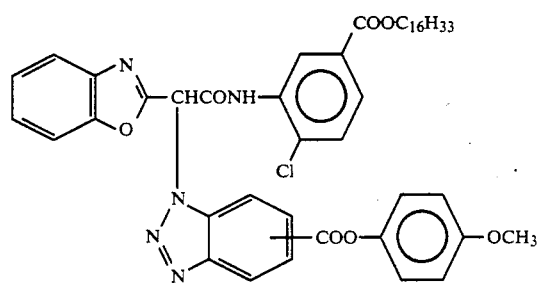

RC-3: (Coupler (2), ibid.)

TABLE 1-continued

| Sample No. | Coupler in 12th Layer | Image Stability (Dmax) | Edge Effect |
| --- | --- | --- | --- |

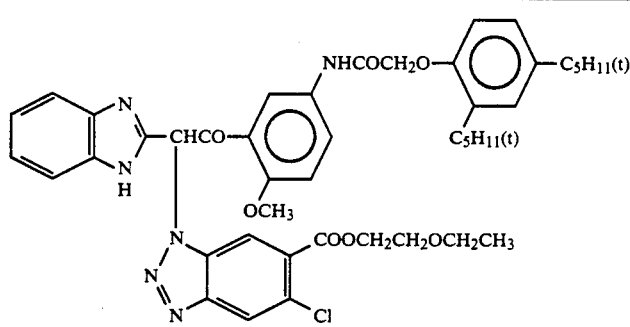

It is apparent from the results in Table 1 that the samples using the coupler according to the present invention are superior to the comparative samples in image stability and edge effect (indicative of sharpness).

EXAMPLE 2

A light-sensitive material was prepared in the same manner as Sample 210 of JP-A-1-269935 was prepared, except for replacing the coupler EX-8 (the same as ExY-9 used in Sample 101 of Example 1 of the present invention) with the same weight of Compound (1), (3), (4), (6), or (9).

Each of the resulting samples was evaluated in the same manner as in Example 1, except for conducting color development processing according to the following procedure.

As a result, the samples using the coupler according to the present invention were proved superior to the comparative sample using EX-8 out of the scope of the present invention in both image stability and sharpness.

Color Development Processing:

| Step | Time | Temp. | Rate of Replenishment* | Volume of Tank |
| --- | --- | --- | --- | --- |
| Color development | 3 min 15 sec | 37.8° C. | 25 ml | 10 l |
| Bleach | 45 sec | 38° C. | 5 ml | 4 l |
| Blix (1) | 45 sec | 38° C. | ** | 4 l |
| Blix (2) | 45 sec | 38° C. | 30 ml | 4 l |
| Washing (1) | 20 sec | 38° C. | ** | 2 l |
| Washing (2) | 20 sec | 38° C. | 30 ml | 2 l |
| Stabilization | 20 sec | 38° C. | 20 ml | 2 l |
| Drying | 1 min | 55° C. | | |

Note:
*Per meter length of 35 mm wide film

In blix step and washing step counter-flow system from (2) to (1) was carried out.

All the overflow from the bleach step was introduced into blix (2).

The amount of the blix solution which was carried over into the washing step was 2 ml/m-35 mm wide film.

| | Running Solution (g) | Replenisher (g) |
| --- | --- | --- |
| Color Developing Solution Formulation: | | |
| Diethylenetriaminepentaacetic acid | 5.0 | 6.0 |
| Sodium sulfite | 4.0 | 5.0 |
| Potassium carbonate | 30.0 | 37.0 |
| Potassium bromide | 1.3 | 0.5 |
| Potassium iodide | 1.2 mg | — |
| Hydroxylamine sulfate | 2.0 | 3.6 |
| 4-[N-Ethyl-N-β-hydroxyethyl-amino]-2-methylaniline sulfate | 4.7 | 6.2 |
| Water to make | 1.0 l | 1.0 l |
| pH | 10.00 | 10.15 |
| Fixing Solution Formulation: | | |
| Ammonium (1,3-diaminopropane-tetraacetato)iron (III) monohydrate | 144.0 | 206.0 |
| 1,3-Diaminopropanetetraacetic acid | 2.8 | 4.0 |
| Ammonium bromide | 84.0 | 120.0 |
| Ammonium nitrate | 17.5 | 25.0 |
| Aqueous ammonia (27%) | 10.0 ml | 1.8 ml |
| Acetic acid (98%) | 51.1 ml | 73.0 ml |
| Water to make | 1.0 l | 1.0 l |
| pH | 4.3 | 3.4 |
| Blix Solution Formulation: | | |
| Ammonium (ethylenediaminetetra-acetato)iron (III) dihydrate | 50.0 | — |
| Disodium ethylenediaminetetra-acetate | 5.0 | 25.0 |
| Ammonium sulfite | 12.0 | 20.0 |
| Aqueous ammonium thiosulfate solution (700 g/l) | 290.0 ml | 320.0 ml |
| Aqueous ammonia (27%) | 6.0 ml | 15.0 ml |
| Water to make | 1.0 l | 1.0 l |
| pH | 6.8 | 8.0 |

Washing Water

The running solution and replenisher had the same composition.

Tap water was passed through a mixed bed column packed with an H-type strongly acidic cation exchange resin ("Amberlite IR-120B" produced by Rohm & Haas) and an OH-type strongly basic anion exchange resin ("Amberlite IRA-400" produced by Rohm & Haas) to reduce both the calcium ion and magnesium ion content to 3 mg/l or less, and 20 mg/l of sodium dichloroisocyanurate and 150 mg/l of sodium sulfate was added to the thus treated water. The resulting washing water had a pH between 6.5 and 7.5.

Stabilizing Solution Formulation

The running water and replenisher had the same composition.

| | |
| --- | --- |
| Formalin (27%) | 1.2 ml |

-continued

| | |
|---|---|
| Surface active agent: | 0.4 g |
| [C$_{10}$H$_{21}$—O–(CH$_2$CH$_2$O)$_{10}$–H] | |
| Ethylene glycol | 1.0 g |
| Water to make | 1.0 l |
| pH | 5.0–7.0 |

While the invention has been described in detail and with reference to specific examples thereof, it will be apparent to one skilled in the art that various changes and modifications can be made therein without departing from the spirit and scope thereof.

What is claimed is:

1. A silver halide color light-sensitive material comprising a support having thereon at least one hydrophilic colloidal layer which contains a DIR coupler represented by formula (I):

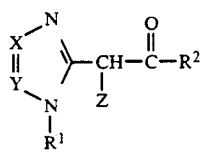
(I)

wherein R$^1$ represents a hydrogen atom, an aliphatic group, an aromatic group, or a heterocyclic group; R$^2$ represents an organic group; X and Y each represent —N= or

wherein R$^3$ represents a hydrogen atom, a halogen atom, a cyano group, a nitro group, an amino group, an acyl group, an acylamino group, a carbamoyl group, a carbamoylamino group, a sulfonyl group, a sulfonylamino group, a sulfamoyl group, a sulfamoylamino group, an alkoxy group, an aryloxy group, an alkoxycarbonyl group, an aryloxycarbonyl group, a hydroxyl group, a sulfenyl group, a sulfinyl group, an aliphatic group, an aromatic group, or a heterocyclic group; and Z represents a releasable group which is released on reacting with an oxidation product of an aromatic primary amine developing agent to become a development inhibitor or a precursor thereof and which diffuses into a color developing solution and then decomposes to a compound having no substantial influence on photographic properties.

2. A silver halide color light-sensitive material as claimed in claim 1, wherein Z represents a group represented by formula (II):

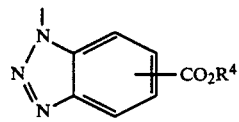
(II)

wherein R$^4$ represents an aliphatic group having from 1 to 4 carbon atoms or a pyridyl group.

3. A silver halide color light-sensitive material as claimed in claim 2, wherein said aliphatic group is a substituted aliphatic group.

4. A silver halide color light-sensitive material as claimed in claim 3, wherein said aliphatic group is substituted with a substituent selected from the group consisting of an alkoxycarbonyl group having from 2 to 6 carbon atoms and a carbamoyl group having from 1 to 7 carbon atoms.

5. A silver halide color light-sensitive material as claimed in claim 2, wherein R$^4$ represents an aliphatic group having from 1 to 3 carbon atoms.

6. A silver halide color light-sensitive material as claimed in claim 5, wherein said aliphatic group is a substituted aliphatic group.

7. A silver halide color light-sensitive material as claimed in claim 6, wherein said substituted aliphatic group is substituted with a substituent selected from the group consisting of an alkoxycarbonyl group having from 2 to 6 carbon atoms and a carbamoyl group having from 1 to 7 carbon atoms.

8. A silver halide color light-sensitive material as claimed in claim 1, wherein said DIR coupler represented by formula (I) is present in an amount of from $1 \times 10^{-7}$ to 0.5 mol per mol of silver present in said hydrophilic colloidal layer or a layer adjacent thereto.

9. A silver halide color light-sensitive material as claimed in claim 8, wherein said DIR coupler represented by formula (I) is present in an amount of from $1 \times 10^{-6}$ to $1 \times 10^{-1}$ mol per mol of silver present in said hydrophilic colloidal layer or a layer adjacent 10. A silver halide color light-sensitive material as claimed in claim 1, wherein said DIR coupler represented by formula (I) is present in combination with at least one known coupler.

11. A silver halide color light-sensitive material as claimed in claim 10, wherein said DIR coupler represented by formula (I) and said at least one known coupler are present in a molar ratio of said compound represented by formula (I) to said at least one known coupler of from 0.1/99.9 to 90/10.

12. A silver halide color light-sensitive material as claimed in claim 11, wherein said molar ratio is from 1/99 to 50/50.

13. A silver halide color light-sensitive material as claimed in claim 1, wherein said material contains silver halide elected from the group consisting of silver iodobromide, silver iodochloride, and silver iodochlorobromide, each having a silver iodide content of at most about 30 mol %.

14. A silver halide color light-sensitive material as claimed in claim 13, wherein said silver halide is selected from the group consisting of silver iodobromide and silver iodochlorobromide having a silver iodide content of from about 2 mol % to about 10 mol %.

* * * * *